(12) United States Patent
Stahly et al.

(10) Patent No.: US 6,605,606 B1
(45) Date of Patent: Aug. 12, 2003

(54) SOLID FORMS OF TIN ETHYL ETIOPURPURIN AND PROCESSES FOR PRODUCING SUCH FORMS

(75) Inventors: G. Patrick Stahly, West Lafayette, IN (US); Barbara A. Garcia, Ventura, CA (US); Byron C. Robinson, Santa Barbara, CA (US)

(73) Assignee: Miravant Pharmaceuticals, Inc., Santa Barbara, CA (US)

( * ) Notice: Subject to any disclaimer, the term of this patent is extended or adjusted under 35 U.S.C. 154(b) by 0 days.

(21) Appl. No.: 09/633,105

(22) Filed: Aug. 4, 2000

(51) Int. Cl.$^7$ ..................... C07D 487/22; A61K 31/555
(52) U.S. Cl. ........................ 514/185; 540/145
(58) Field of Search ........................... 540/145; 514/185

(56) References Cited

U.S. PATENT DOCUMENTS 5,051,415 A    9/1991   Morgan et al. ............. 514/185

FOREIGN PATENT DOCUMENTS

EP         0 256 036 B1      4/1993
WO         WO-96/32094    *  10/1996

OTHER PUBLICATIONS

Morgan et al Proceedings of the Society of Photo–Optical Instrumentation Engineers 847 (1987) 172–179.*
PCT International Search Report.
Morgan et al., *New Photosensitizers For Photdynamic Therapy*: combined Effect of Metallopurpurin derivatives and Light on Transplantable Bladder Tumors, 48 American Association for Cancer Research 194–198 (1988).
Pogue et al., Photophysical Properties of Tin Ethyl Etiopurpurin I (SnET2) and Tin Octaethylbenzochlorin (SnOEBC) in Solution and Bound to Albumin, 68 Photochemistry and Photobiology 809–815 (1988).
Kaplan et al., *Photdynamic Therapy in the AManagement of Metastic Cutaneous Adenocarcinomas*: Case Reports from Phase 1/2 Studies Using Tin Ethyl Etiopurpurin (SnET2), 67 Journal of Surgical Oncology 121–125 (1998).
Allison et al., Tin Ethyl Etiopurpurin–Induced Photodynamic Therapy for the Treatment of Human Immunodeficiency Virus–Associated *Kaposi's Sarcoma*, 59 Current Therapeutic Research 23–27 (1998).

* cited by examiner

Primary Examiner—Mark L Berch
Assistant Examiner—Kahsay Habte
(74) Attorney, Agent, or Firm—Finnegan, Henderson, Farabow, Garrett & Dunner, L.L.P.

(57) ABSTRACT

Solid forms of tin ethyl etiopurpurin (SnET2), including crystalline form I, crystalline Form II, disordered Form II, and an amorphous form are disclosed. Also disclosed are the 1,2-dichloroethane solvate of SnET2 and the N,N-dimethylformamide solvate of SnET2. These solid forms of SnET2 are useful as pharmaceuticals that exhibit pharmacological activity when irradiated with light and thus are useful in photodynamic therapy. Also disclosed are methods for making these solid forms of SnET2 and pharmaceuticals including these solid forms of SnET2.

77 Claims, 11 Drawing Sheets

SOLID FORMS OF TIN ETHYL ETIOPURPURIN AND PROCESSES FOR PRODUCING SUCH FORMS

FIELD OF THE INVENTION

The present invention relates to compounds and methods for producing compounds that are useful as photoselective compounds in photodynamic therapy. Specifically, the invention is directed to solid forms of tin ethyl etiopurpurin and their production and isolation.

BACKGROUND OF THE INVENTION

Tin ethyl etiopurpurin, which has the name (OC-6-13) Dichloro[rel-ethyl (18R, 19S)-3,4,20,21-tetradehydro-4,9, 14,19-tetraethyl-18,19-dihydro-3,8,13,18-tetramethyl-20-phorbinecarboxalato(2-)-$\kappa N^{23}$, $\kappa N^{24}$, $\kappa N^{25}$, $\kappa N^{26}$]tin, or "SnET2", has the following structure.

SnET2

SnET2 as described and claimed in U.S. Pat. No. 5,051, 415 (Sep. 24, 1991) shows potent pharmacological activity when irradiated with light and may be used in photodynamic therapy for the treatment and diagnosis of a range of diseases.

The solid forms of SnET2 are particularly important because they enable SnET2 to be conveniently manufactured, purified, transported and formulated in, for example, tablets or capsules or any other type of dosage form such as lozenges or rapidly dissolving tablets for oral administration, suspensions for oral administration, or other formulation such as suppositories, or topical formulations, or dissolved in suitable solvents as a solution or any other formulation for parenteral or topical administration.

However, the present inventors are not aware of any work by others to produce, isolate, or characterize solid forms of SnET2.

Accordingly, there is a need to produce SnET2 in a pure and highly crystalline form to fulfill exacting pharmaceutical requirements and specifications and to meet regulatory requirements for approval and marketing.

The crystalline forms of SnET2 are of particular interest since they are more stable than the amorphous forms. There may, however, also be advantages to producing SnET2 in an amorphous solid form to achieve the solubility advantages of this form.

There is also a need for a process for producing SnET2 that is convenient to operate on a plant scale. In particular, it is desirable that the solid forms of SnET2 be prepared with convenient solvents and that the solvents be readily recoverable.

In addition, the product should be in a form that is readily filtered off and easily dried. It also is desirable that the product can be recrystallized from the same solvent system used to prepare the original form.

SUMMARY OF THE INVENTION

The present inventors have produced and isolated SnET2 in two crystalline forms designated crystalline Form I and crystalline Form II, and in an amorphous form. The crystalline forms can be prepared by, for example, crystallization or slurrying in various solvents. These forms have the desirable feature of being easily filterable and dried and have advantageous properties with respect to the manufacturing process. In addition, they have consistent X-ray diffraction patterns which provides a convenient means of control. Furthermore, crystalline Form II is more stable than crystalline Form I and crystalline Form I can be converted to both crystalline and disordered Form II by, for example, slurrying in dichloromethane, acetone, and mixtures. The amorphous form can be prepared, for example, by grinding either of the crystalline forms.

In addition, the process by which SnET2 is produced often yields a disordered form of crystalline Form II, hereinafter referred to as disordered Form II. This form has the desirable feature of being easily filterable and dried and has advantageous properties with respect to the manufacturing process. It also has a consistent X-ray diffraction pattern which provides a convenient means of control. As used herein in the specification and claims, the term "Form II" refers to both crystalline Form II and disordered Form II.

SnET2 may also be obtained in two solvates (1,2-dichloroethane and dimethylformamide). These forms have the desirable feature of being easily filterable and dried and have advantageous properties with respect to the manufacturing process. In addition, they have consistent X-ray diffraction patterns which provides a convenient means of control.

Additional advantages of the invention will be set forth in the detailed description which follows, and in part will be obvious from the description, or may be learned by practice of the invention. The advantages of the invention can be realized and attained by means of the elements and combinations particularly pointed out in the appended claims.

DETAILED DESCRIPTION OF THE PREFERRED EMBODIMENTS

Unsolvated, anhydrous, polymorphic forms of a compound differ in their free energies. A set of polymorphs may be ranked in order of thermodynamic stability under a given set of pressure and temperature conditions. Thus, given a pathway for interconversion, less stable forms will transform to the most stable form when equilibrium is attained. Production of the stable form is said to occur under thermodynamic conditions. It is frequently the case that a thermodynamically less stable form (or forms) will grow faster than the most stable form. This phenomenon was expressed by Ostwald in the rule of stages, which states that in passing from a less stable state (liquid) into a more stable state (crystalline), the product state is not the most stable state available, but is the nearest in energy to the starting state [W. Ostwald, *Zeits. f. Phys. Chem.* 22:306 (1897)]. Therefore, it is often possible to consistently obtain a less stable form by crystallization under conditions that do not provide enough energy for interconversion of the initial product into the more stable product. Production of the less stable (metastable) form is said to occur under kinetic conditions. Kinetic and thermodynamic conditions differ in the amount of energy utilized. While the absolute amount depends on the compound in question, relatively speaking, kinetic conditions involve lower temperatures and shorter reaction times while thermodynamic conditions involve higher temperatures and longer reaction times.

Figure 1:
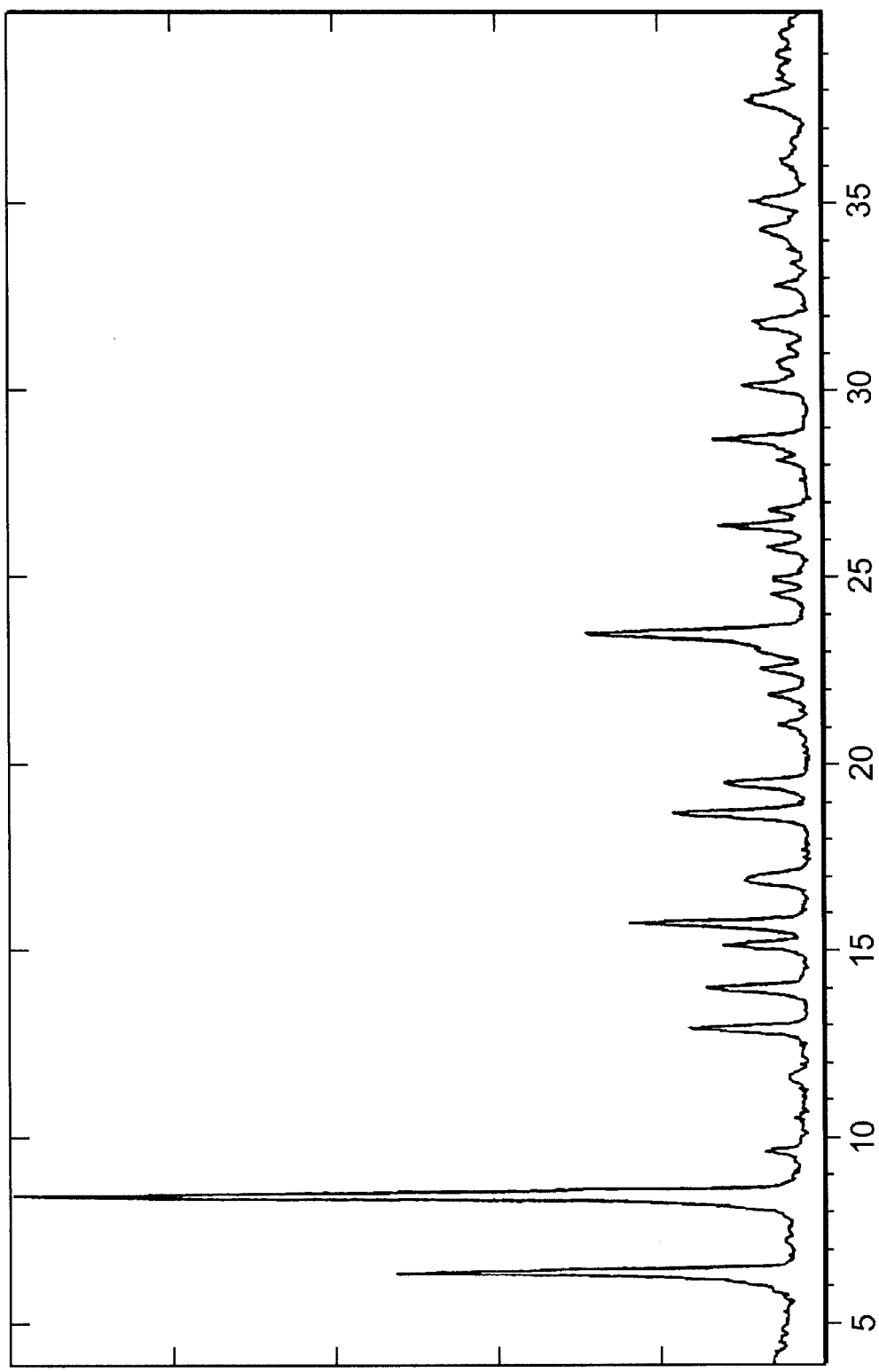
FIG. 1 illustrates the X-Ray Diffraction Pattern of Crystalline Form I of SnET2.
Figure 2:
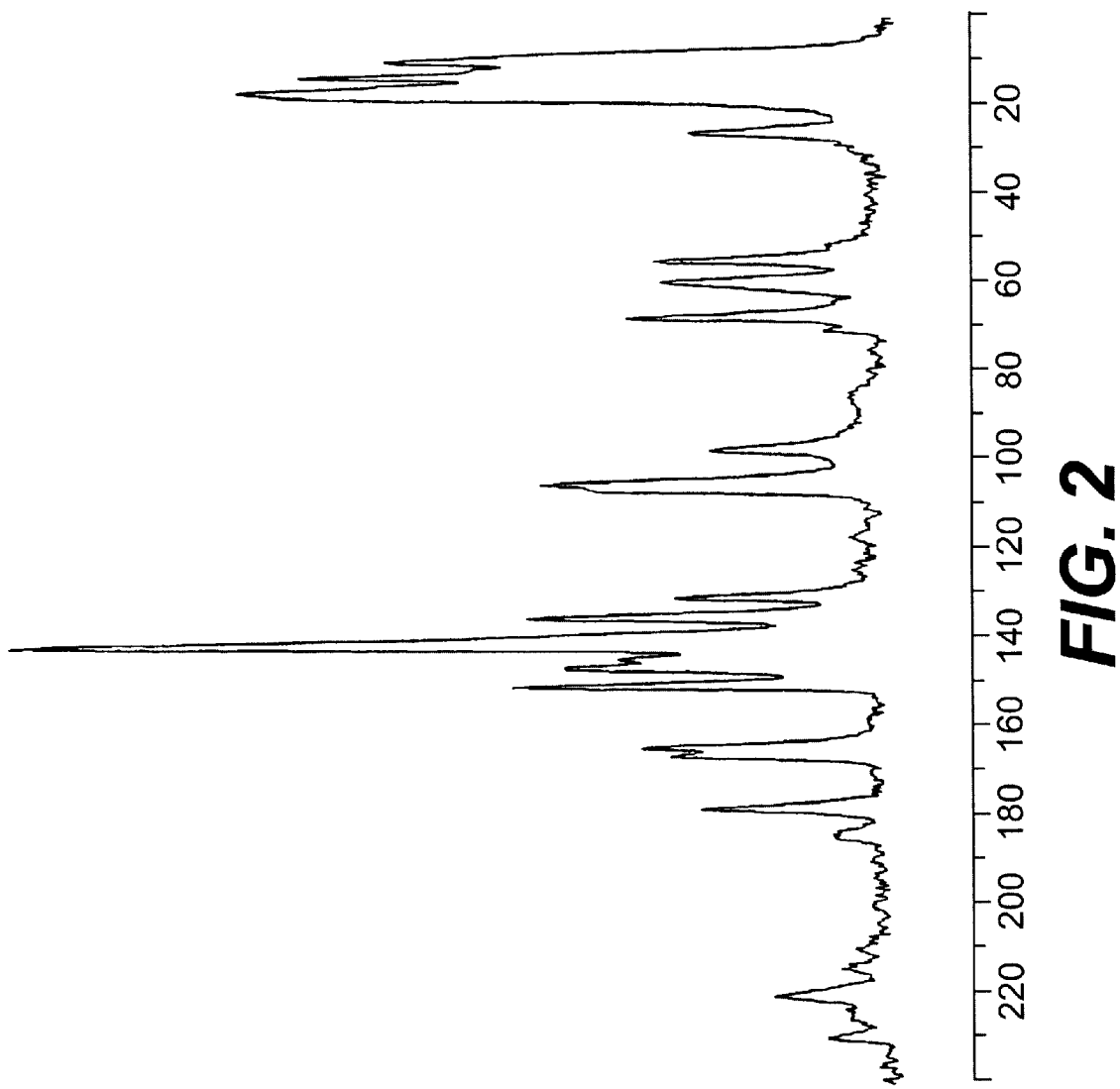
FIG. 2 illustrates the Solid State NMR Spectrum of Crystalline Form I of SnET2.

Crystalline Form I of SnET2, most readily formed under kinetic conditions, may be characterized by its X-ray diffraction pattern and solid state NMR spectrum as shown in FIGS. 1 and 2, respectively. Referring to FIG. 1, the X-ray diffraction pattern was measured using a Siemens D-500 Diffraktometer-Kristalloflex with an IBM-compatible interface, software=DIFFRAC AT (SOCABIM 1986, 1992). CuKα radiation (20 mA, 40 kV, λ=1.5406 Å) (Slits I and II at 1°) was electronically filtered by the Kevex Psi Peltier Cooled Silicon [Si(Li)] Detector (Slits: III at 1°, IV at 0.15°). Referring to FIG. 2, the solid state NMR spectrum was measured on a Bruker AC 250 mHz spectrometer using high-power proton decoupling and cross-polarization (CP) with magic-angle spinning (MAS) at approximately 5 KHz. The magic-angle was adjusted using the spinning sidebands of the $^{79}$Br signal of solid KBr according to the method of Frye and Maciel (Frye, J. S. and Maciel, G. E. J. Magn. Reson. (1982) 48, 125–31). Approximately 250–300 mg of sample was packed into a suitable rotor. Chemical shifts are relative to an appropriate external standard, which is tetrakis(trimethylsilyl)silane (methyl signal at 3.50 ppm).

In x-ray powder diffraction analysis, the angle at which a reflection is observed is related to an interatomic distance by the Bragg equation: $n\lambda=2d \sin \theta$, where n is an integer, λ is the wavelength of the x-rays used, d is the perpendicular distance between atomic lattice planes in the crystal which "reflect" the x-rays, and θ is the complement of the angle of incidence of the x-ray beam with the sample. X-rays are actually diffracted by atoms in a crystal rather than reflected, but the positions of the diffracted beams can be predicted by considering that they are reflected from atomic lattice planes using the Bragg equation. 2θ values are given in degrees and d values are in angstroms.

As used in the Tables herein, 2θ values are given in degrees, "d-spacings" or "d" values are given in angstroms, and relative intensities (Rel. I) are given in %.

Table 1 lists the 2θ values, "d-spacings" shown as "d," and relative intensities of the major lines in the diffraction pattern of crystalline Form I.

TABLE 1

Intensities and Peak Locations of All Major Diffraction Lines in Crystalline Form I.

| 2θ | d | Rel. I (>9%) |
|---|---|---|
| 6.5 | 13.5 | 52 |
| 8.6 | 10.3 | 100 |
| 12.9 | 6.8 | 17 |
| 14.0 | 6.3 | 15 |
| 15.2 | 5.8 | 12 |
| 15.7 | 5.6 | 24 |
| 16.9 | 5.2 | 10 |
| 18.7 | 4.8 | 19 |
| 19.5 | 4.6 | 12 |
| 23.0 | 3.9 | 10 |
| 23.4 | 3.8 | 29 |
| 26.3 | 3.4 | 13 |
| 28.6 | 3.1 | 14 |
| 30.0 | 3.0 | 10 |
| 37.6 | 2.4 | 9 |

Table 2 lists the solid state NMR chemical shifts of crystalline Form I. The chemical shifts are determined by reference to an external standard, which is tetrakis(trimethylsilyl)silane (methyl signal at 3.50 ppm). In some cases the error in these chemical shifts can be introduced by variations in instrument configuration and external standards. For this reason the chemical shifts are also reported as the difference (delta) between the resonance at the lowest ppm and all other resonances. In this way the deltas are independent of instrument variations and external standards and are more accurate.

TABLE 2

Solid state NMR chemical shifts of crystalline Form I. The column labeled delta reports the chemical shifts relative to the lowest field signal.

| Chemical Shift (ppm) | Delta (ppm) |
|---|---|
| 177.5 | 168.1 |
| 165.6 | 156.2 |
| 163.8 | 154.4 |
| 149.8 | 140.4 |
| 145.5 | 136.1 |
| 143.8 | 134.4 |
| 140.4 | 131 |
| 134.4 | 125 |
| 130.1 | 120.7 |
| 104 | 94.6 |
| 97 | 87.6 |
| 67.1 | 57.7 |
| 58.9 | 49.5 |
| 54.2 | 44.8 |
| 25.6 | 16.2 |
| 16.1 | 6.7 |
| 12.8 | 3.4 |
| 9.4 | 0 |

Figure 3:
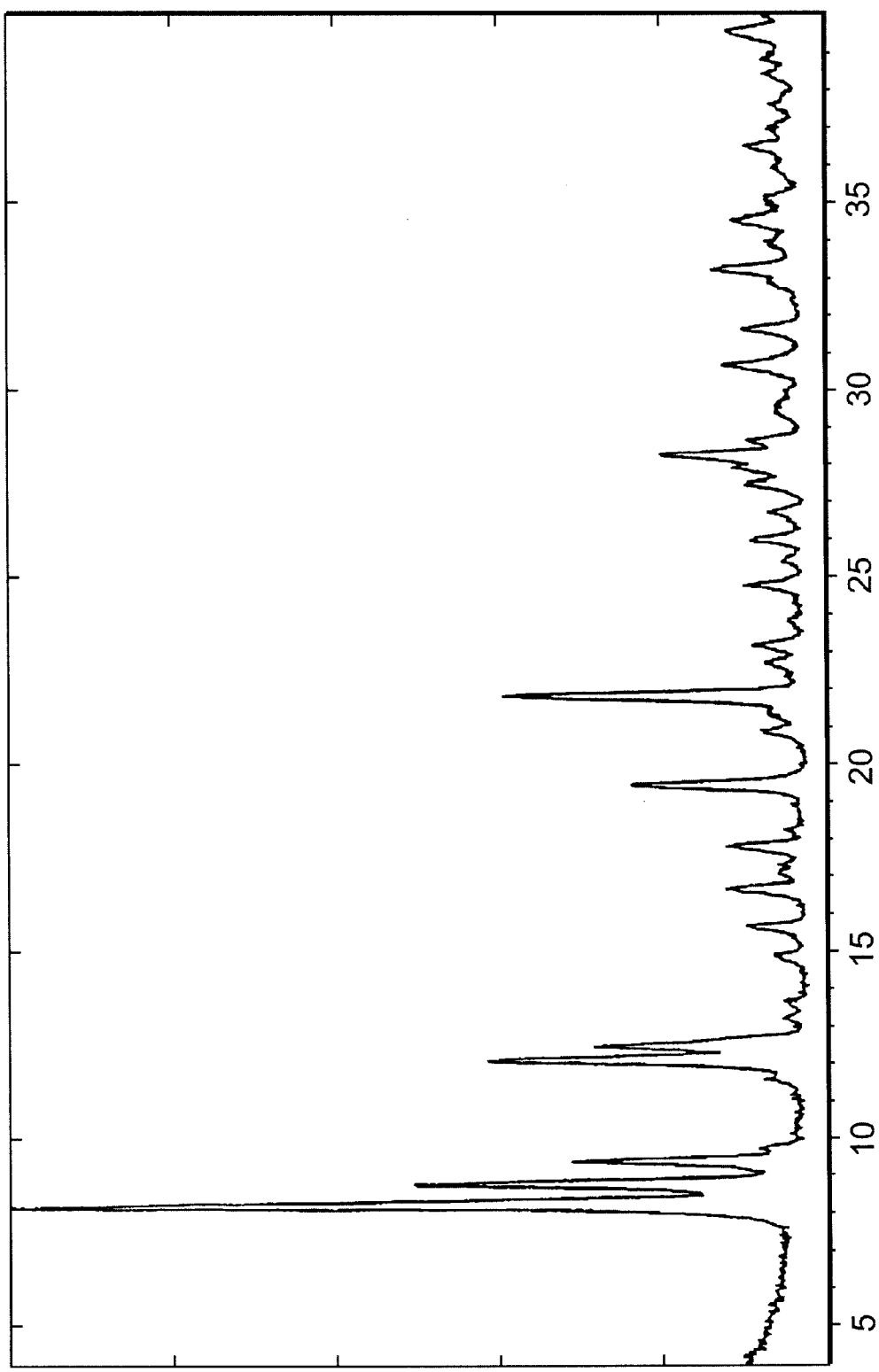
FIG. 3 illustrates the X-Ray Diffraction Pattern of Crystalline Form II of SnET2.
Figure 4:
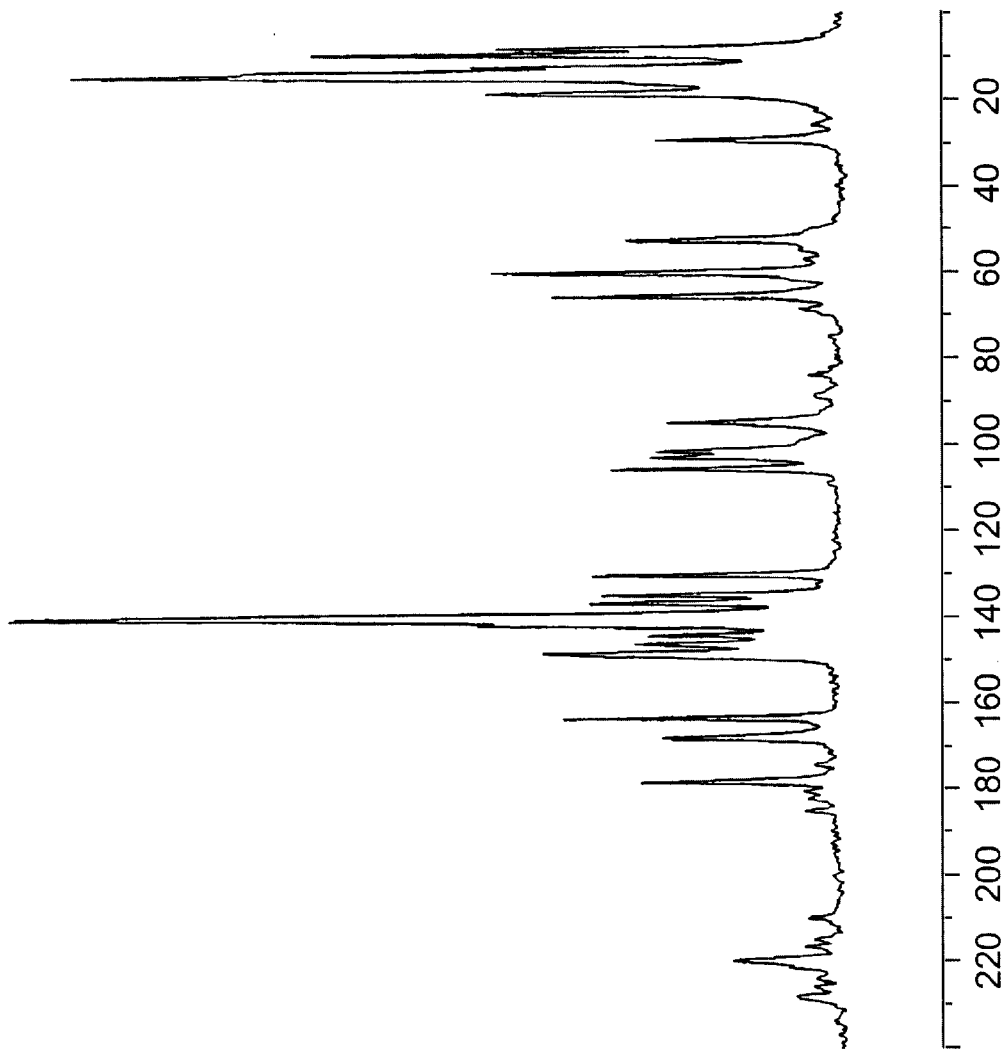
FIG. 4 illustrates the Solid State NMR Spectrum of Crystalline Form II of SnET2.

Crystalline Form II of SnET2, the thermodynamically more stable form, may be characterized by its X-ray diffraction pattern and solid state NMR spectrum as shown in FIGS. 3 and 4, respectively. Referring to FIG. 3, the X-ray diffraction pattern was measured using a Siemens D-500 Diffraktometer-Kristalloflex with an IBM-compatible interface, software=DIFFRAC AT (SOCABIM 1986, 1992). CuKα radiation (20 mA, 40 kV, λ=1.5406 Å) (Slits I and II at 1°) was electronically filtered by the Kevex Psi Peltier Cooled Silicon [Si(Li)] Detector (Slits: III at 1°, IV at 0.15°). Referring to FIG. 4, the solid state NMR spectrum was measured on a Bruker AC 250 mHz spectrometer using high-power proton decoupling and cross-polarization (CP) with magic-angle spinning (MAS) at approximately 5 KHz. The magic-angle was adjusted using the spinning sidebands of the $^{79}$Br signal of solid KBr according to the method of Frye and Maciel (Frye, J. S. and Maciel, G. E. J. Magn. Reson. (1982) 48, 125–31). Approximately 250–300 mg of sample was packed into a suitable rotor. Chemical shifts are relative to an appropriate external standard, which is tetrakis (trimethylsilyl)silane (methyl signal at 3.50 ppm).

Table 3 lists the 2θ values, "d-spacings", relative intensities and peak width at half height of the major lines in the diffraction pattern of crystalline Form II.

TABLE 3

Intensities, peak locations and peak width at half height (PWHH) of all major diffraction lines in crystalline Form II.

| 2θ | d | Rel. I (>10%) | PWHH (° 2θ) |
|---|---|---|---|
| 8.4 | 10.6 | 100 | 0.23 |
| 8.9 | 10.0 | 51 | 0.22 |
| 9.5 | 9.4 | 31 | 0.23 |
| 12.2 | 7.3 | 42 | 0.21 |
| 12.5 | 7.1 | 29 | 0.28 |
| 16.7 | 5.3 | 12 | 0.22 |
| 17.8 | 5.0 | 12 | 0.22 |
| 19.5 | 4.6 | 24 | 0.30 |
| 21.8 | 4.1 | 39 | 0.28 |
| 27.9 | 3.2 | 11 | 0.22 |
| 28.2 | 3.2 | 20 | 0.25 |
| 30.6 | 2.9 | 13 | 0.29 |
| 33.2 | 2.7 | 14 | 0.29 |
| 34.5 | 2.6 | 11 | 0.31 |
| 39.5 | 2.3 | 12 | 0.33 |

TABLE 4

Solid state NMR chemical shifts of crystalline Form II. The column labeled delta reports the chemical shifts relative to the lowest field signal.

| Chemical Shift (ppm) | Delta (ppm) |
|---|---|
| 178.7 | 170.0 |
| 168.0 | 159.3 |
| 163.6 | 154.9 |
| 148.5 | 139.8 |
| 146.3 | 137.6 |
| 144.3 | 135.6 |
| 141.8 | 133.1 |
| 140.1 | 131.4 |
| 137.1 | 128.4 |
| 135.2 | 126.5 |
| 130.4 | 121.7 |
| 105.9 | 97.2 |
| 103.0 | 94.3 |
| 101.6 | 92.9 |
| 95.1 | 86.4 |
| 66.3 | 57.6 |
| 60.6 | 51.9 |
| 53.3 | 44.6 |
| 29.8 | 21.1 |
| 19.4 | 10.7 |
| 15.1 | 6.4 |
| 12.9 | 4.2 |
| 10.1 | 1.4 |
| 8.7 | 0 |

Figure 5:
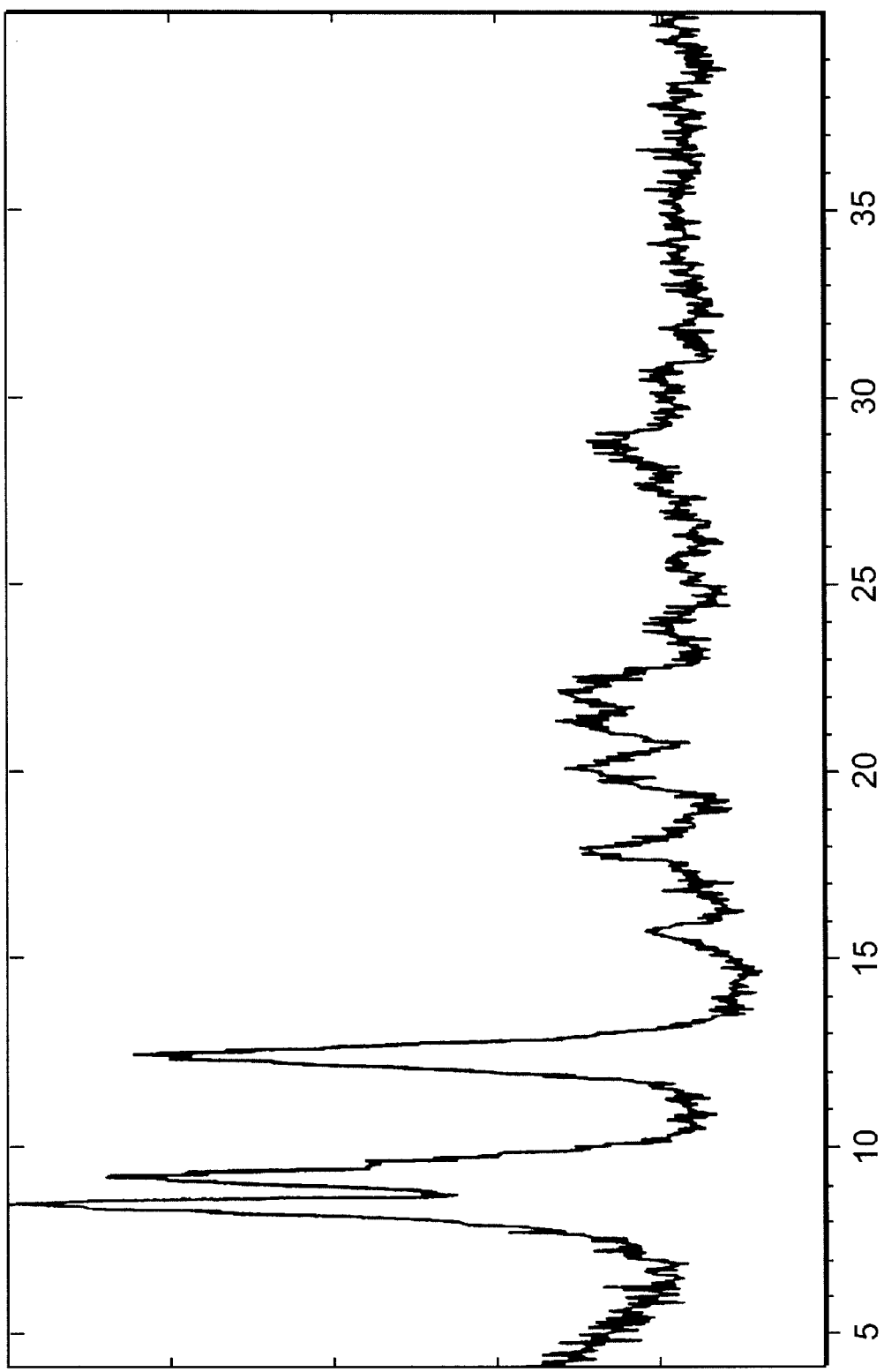
FIG. 5 illustrates the X-Ray Diffraction Pattern of Disordered Form II of SnET2.
Figure 6:
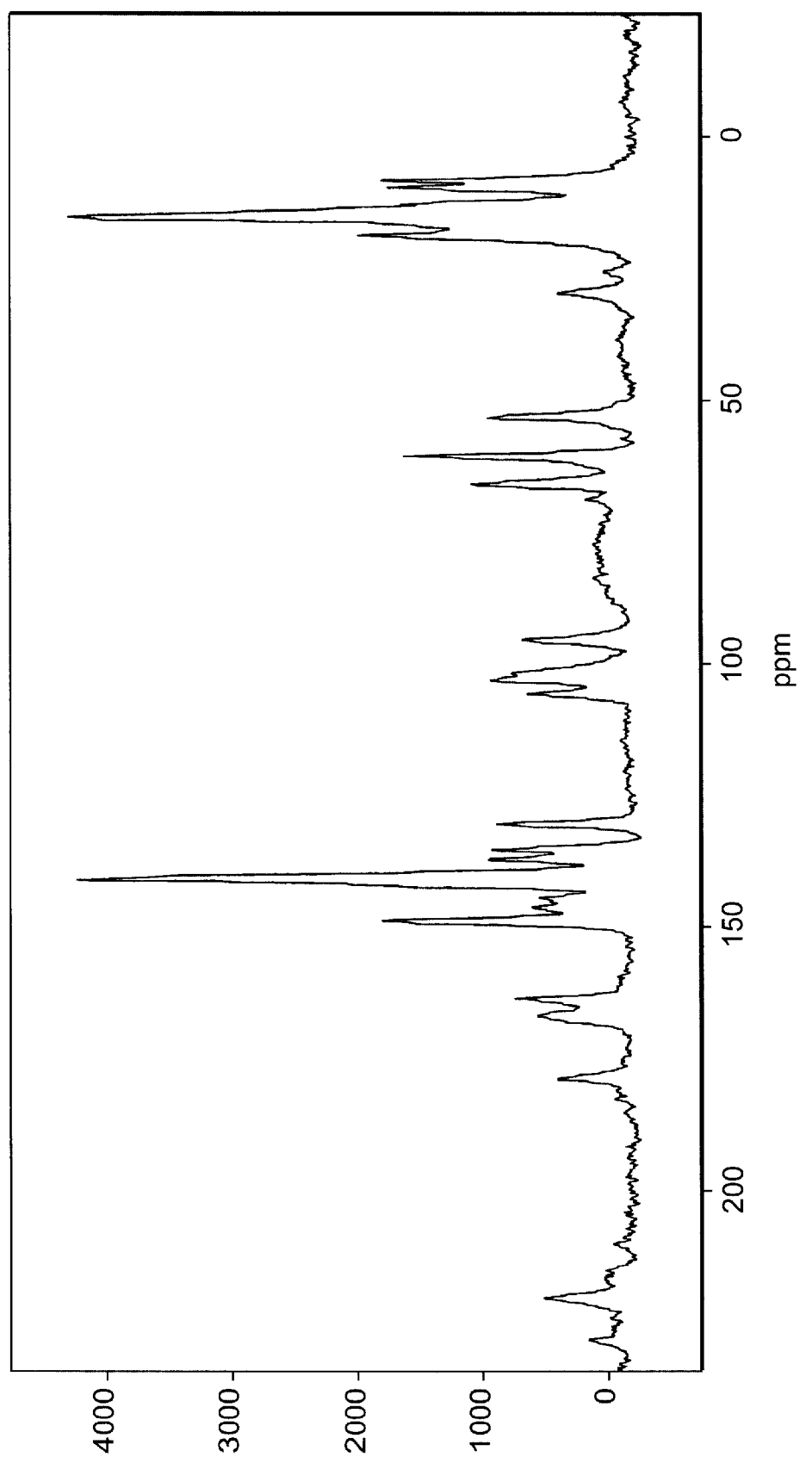
FIG. 6 illustrates the Solid State NMR Spectrum of Disordered Form II of SnET2.

Disordered Form II of SnET2 may be characterized by its X-Ray diffraction pattern and solid state NMR spectrum as shown in FIGS. 5 and 6, respectively. Referring to FIG. 5, the X-ray diffraction pattern was measured using a Siemens D-500 Diffraktometer-Kristalloflex with an IBM-compatible interface, software=DIFFRAC AT (SOCABIM 1986, 1992). CuKα radiation (20 mA, 40 kV, λ=1.5406 Å) (Slits I and II at 1°) was electronically filtered by the Kevex Psi Peltier Cooled Silicon [Si(Li)] Detector (Slits: III at 1°, IV at 0.15°). Referring to FIG. 6, the solid state NMR spectrum was measured on a Bruker AM 250 mHz spectrometer using high-power proton decoupling and cross-polarization (CP) with magic-angle spinning (MAS) at approximately 5 KHz. The magic-angle was adjusted using the spinning sidebands of the $^{79}$Br signal of solid KBr according to the method of Frye and Maciel (Frye, J. S. and Maciel, G. E. J. Magn. Reson. (1982) 48, 125–31). Approximately 250–300 mg of sample was packed into a suitable rotor. Chemical shifts are relative to an appropriate external standard, which is adamantane (methylene signal at 38.5 ppm).

Table 5 lists the 2θ values, "d-spacings", relative intensities, and peak width at half height of the major broad lines in the diffraction pattern of disordered Form II.

TABLE 5

Intensities, peak locations and peak width at half height (PWHH) of all major broad diffraction lines in disordered Form II.

| 2θ Broad peak maxima centered between: | d | Rel. I | PWHH (° 2θ) |
|---|---|---|---|
| 7.5–8.5 | 10.6 | 100 | 0.39 |
| 8.5–10.5 | 9.8 | 88 | 0.64 |
| 11.5–13.5 | 7.2 | 85 | 0.65 |
| 15.0–16.0 | 5.7 | 22 | 0.41 |
| 17.0–19.0 | 5.0 | 30 | 0.63 |
| 19.0–20.5 | 4.4 | 32 | 0.63 |
| 20.5–21.5 | 4.2 | 33 | 0.89 |
| 21.5–23.0 | 4.0 | 33 | 0.80 |
| 23.0–24.5 | 3.7 | 24 | 0.77 |
| 24.5–26.0 | 3.5 | 23 | 0.76 |
| 27.0–28.0 | 3.2 | 26 | 0.73 |
| 28.0–29.5 | 3.1 | 32 | 0.80 |
| 29.5–31.0 | 2.9 | 25 | 1.28 |
| 31.0–32.5 | 2.8 | 22 | 0.66 |

Comparison of the diffractogram patterns exhibited by crystalline and disordered Form II indicate comparable 2θ values. In a perfect crystal, the spacing between atomic lattice planes would be consistent throughout, and each diffraction peak would occur at a single angular value (2θ). Peaks in an x-ray powder diffraction pattern of a sample of perfect crystals would be single, narrow lines. Real crystals are not perfect, but contain molecular packing imperfections which result in sight variations in lattice plane spacings. The consequence is that each spacing encompasses a small range of distances which translate, via the Bragg equation, to diffraction occurring over a small range of angular values. Thus, peaks in x-ray powder diffraction patterns of real samples have width. The wider the peaks, the more disordered are the crystals in the sample. SnET2 can be obtained as crystalline Form II or disordered Form II. Each has the same crystal structure, but they differ in degree of packing disorder.

TABLE 6

Solid state NMR chemical shifts of disordered Form II. The column labeled delta reports the chemical shifts relative to the lowest field signal.

| Chemical Shift (ppm) | Delta (ppm) |
| --- | --- |
| 178.7 | 170.2 |
| 166.6 | 158.1 |
| 163.4 | 154.9 |
| 148.6 | 140.1 |
| 146.3 | 137.8 |
| 144.2 | 135.7 |
| 140.2 | 131.7 |
| 136.9 | 128.4 |
| 135.0 | 126.5 |
| 130.3 | 121.8 |
| 105.6 | 97.1 |
| 102.8 | 94.3 |
| 101.6 | 93.1 |
| 95.2 | 86.7 |
| 68.9 | 60.4 |
| 65.7 | 57.2 |
| 60.4 | 51.9 |
| 53.0 | 44.5 |
| 29.9 | 21.4 |
| 25.6 | 17.1 |
| 19.1 | 10.6 |
| 15.1 | 6.6 |
| 9.9 | 1.4 |
| 8.5 | 0 |

Comparison of the solid-state NMR chemical shifts exhibited by crystalline and disordered Form II indicate comparable delta values. The peaks are broader in the spectrum of disordered Form II than in the spectrum of crystalline Form II, consistent with variations in atomic environments which are introduced on disruption of crystalline order. Broad peaks hamper precise location of peak positions, and lead to small variations in the ppm values obtained for crystalline and disordered Form II.

Figure 7:
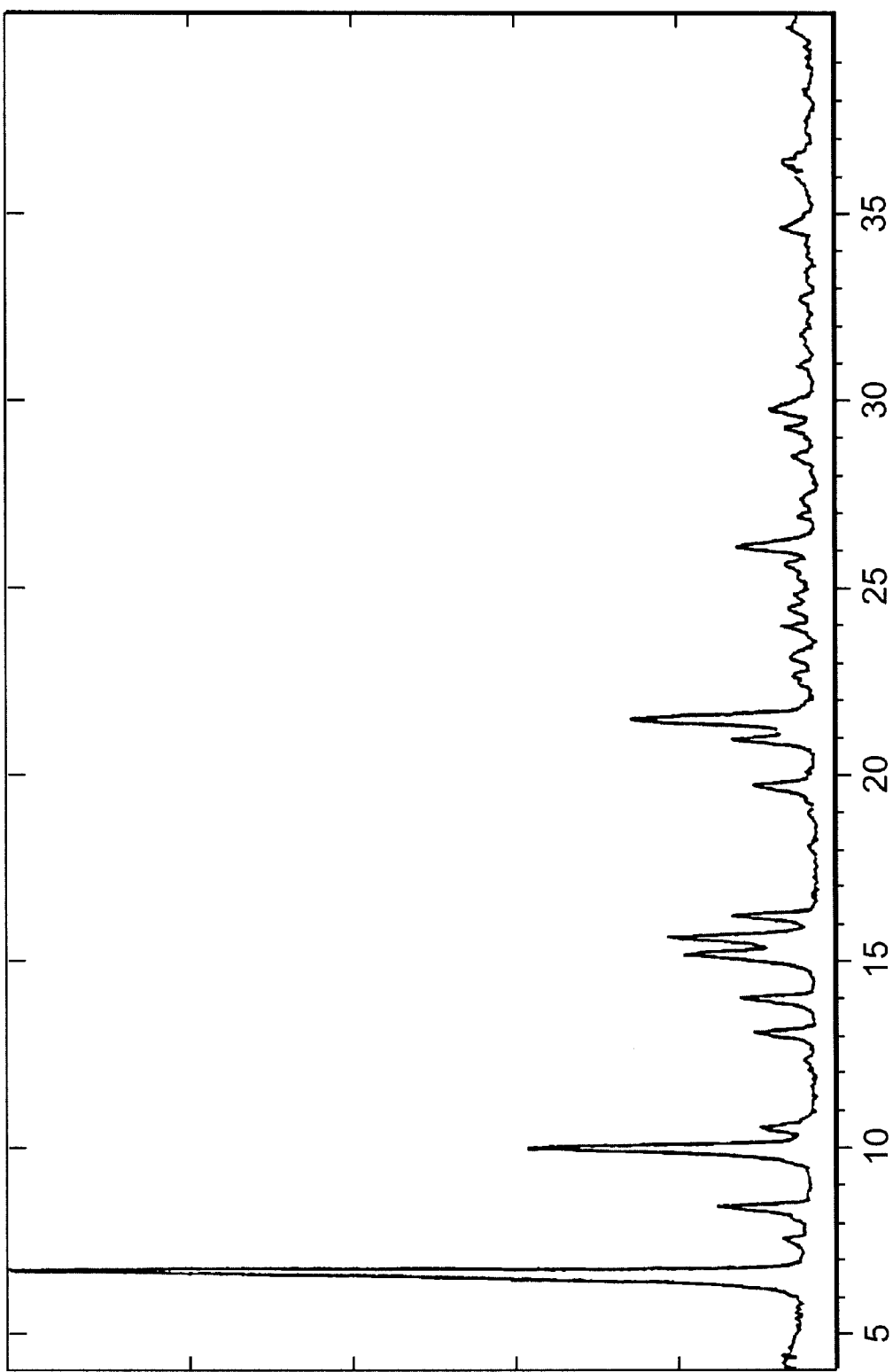
FIG. 7 illustrates the X-Ray Diffraction Pattern of the 1,2-Dichloroethane Solvate of SnET2.
Figure 8:
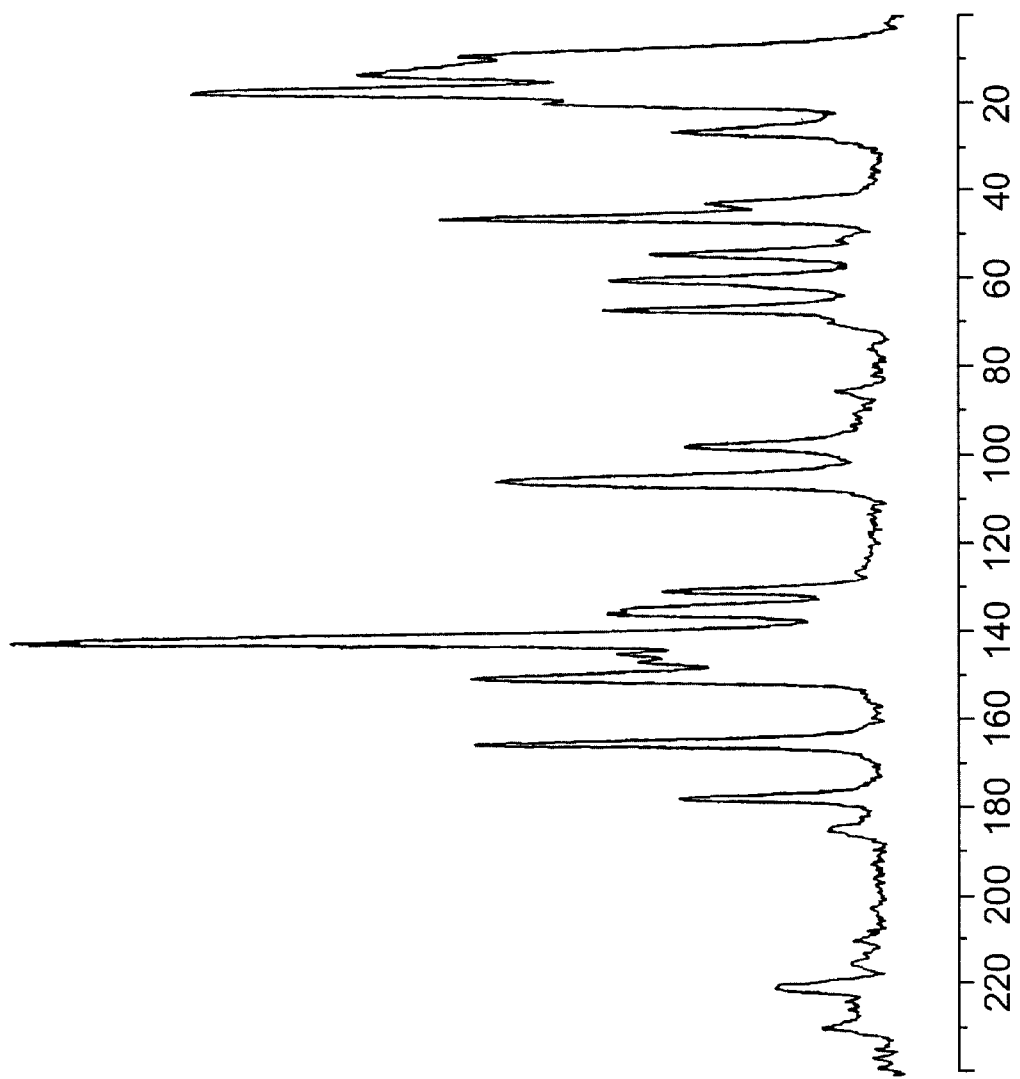
FIG. 8 illustrates the Solid State NMR Spectrum of the 1,2-Dichloroethane Solvate of SnET2.

The 1,2-dichloroethane, or DCE, solvate of SnET2 may be characterized by the fact that it crystallizes with approximately one mole of 1,2-dichloroethane and by its X-ray diffraction pattern and solid state NMR spectrum as shown in FIGS. 7 and 8, respectively. Referring to FIG. 7, the X-ray diffraction pattern was measured using a Siemens D-500 Diffraktometer-Kristalloflex with an IBM-compatible interface, software=DIFFRAC AT (SOCABIM 1986, 1992). CuK$\alpha$ radiation (20 mA, 40 kV, $\lambda$=1.5406 Å) (Slits I and II at 1°) was electronically filtered by the Kevex Psi Peltier Cooled Silicon [Si(Li)] Detector (Slits: III at 1°, IV at 0.15°). Referring to FIG. 8, the solid state NMR spectrum was measured on a Bruker AC 250 mHz spectrometer using high-power proton decoupling and cross-polarization (CP) with magic-angle spinning (MAS) at approximately 5 KHz. The magic-angle was adjusted using the spinning sidebands of the $^{79}$Br signal of solid KBr according to the method of Frye and Maciel (Frye, J. S. and Maciel, G. E. *J. Magn. Reson.* (1982) 48, 125–31). Approximately 250–300 mg of sample was packed into a suitable rotor. Chemical shifts are relative to an appropriate external standard, which is tetrakis(trimethylsilyl)silane (methyl signal at 3.50 ppm).

Table 7 lists the 2$\theta$ values, "d-spacings", and relative intensities of the major lines in the diffraction pattern of the 1,2-dichloroethane solvate of SnET2.

TABLE 7

Intensities and peak locations of all major diffraction lines in the 1,2-dichloroethane solvate of SnET2.

| 2$\theta$ | d | Rel. I |
| --- | --- | --- |
| 6.6 | 13.4 | 100 |
| 7.5 | 11.8 | 6 |
| 8.4 | 10.6 | 14 |
| 10.0 | 8.9 | 36 |
| 10.5 | 8.4 | 9 |
| 13.1 | 6.8 | 9 |
| 13.9 | 6.3 | 11 |
| 15.1 | 5.9 | 18 |
| 15.5 | 5.7 | 20 |
| 16.2 | 5.5 | 12 |
| 19.7 | 4.5 | 9 |
| 20.9 | 4.2 | 12 |
| 21.4 | 4.1 | 25 |
| 24.4 | 3.6 | 5 |
| 26.0 | 3.4 | 11 |
| 28.4 | 3.1 | 4 |
| 29.1 | 3.1 | 5 |
| 29.7 | 3.0 | 7 |
| 34.5 | 2.6 | 6 |

TABLE 8

Solid state NMR chemical shifts of the 1,2-dichloroethane solvate of SnET2. The column labeled delta reports the chemical shifts relative to the lowest field signal.

| Chemical Shift (ppm) | Delta (ppm) |
| --- | --- |
| 176.8 | 167.8 |
| 164.6 | 155.6 |
| 149.4 | 140.4 |
| 145.8 | 136.8 |
| 143.9 | 134.9 |
| 140.6 | 131.6 |
| 134.8 | 125.8 |
| 133.9 | 124.9 |
| 129.9 | 120.9 |
| 104.6 | 95.6 |
| 97.1 | 88.1 |
| 66.5 | 57.5 |
| 59.6 | 50.6 |
| 53.9 | 44.9 |
| 45.7 | 36.7 |
| 42.7 | 33.7 |
| 26 | 17 |
| 19.7 | 10.7 |
| 16.9 | 7.9 |
| 12.8 | 3.8 |
| 9 | 0 |

Figure 9:
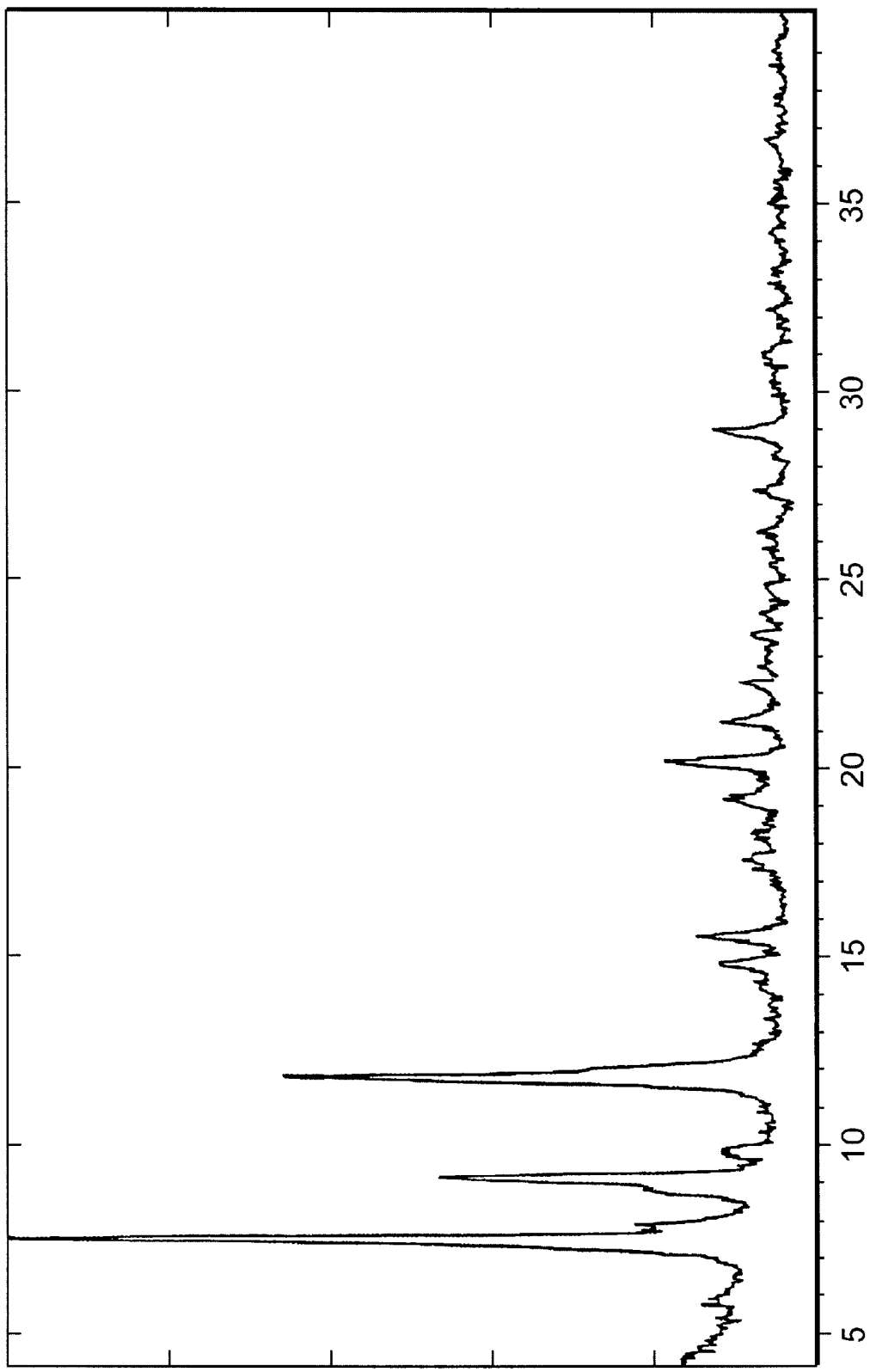
FIG. 9 illustrates the X-Ray Diffraction Pattern of the N,N-Dimethylformamide Solvate of SnET2.
Figure 10:
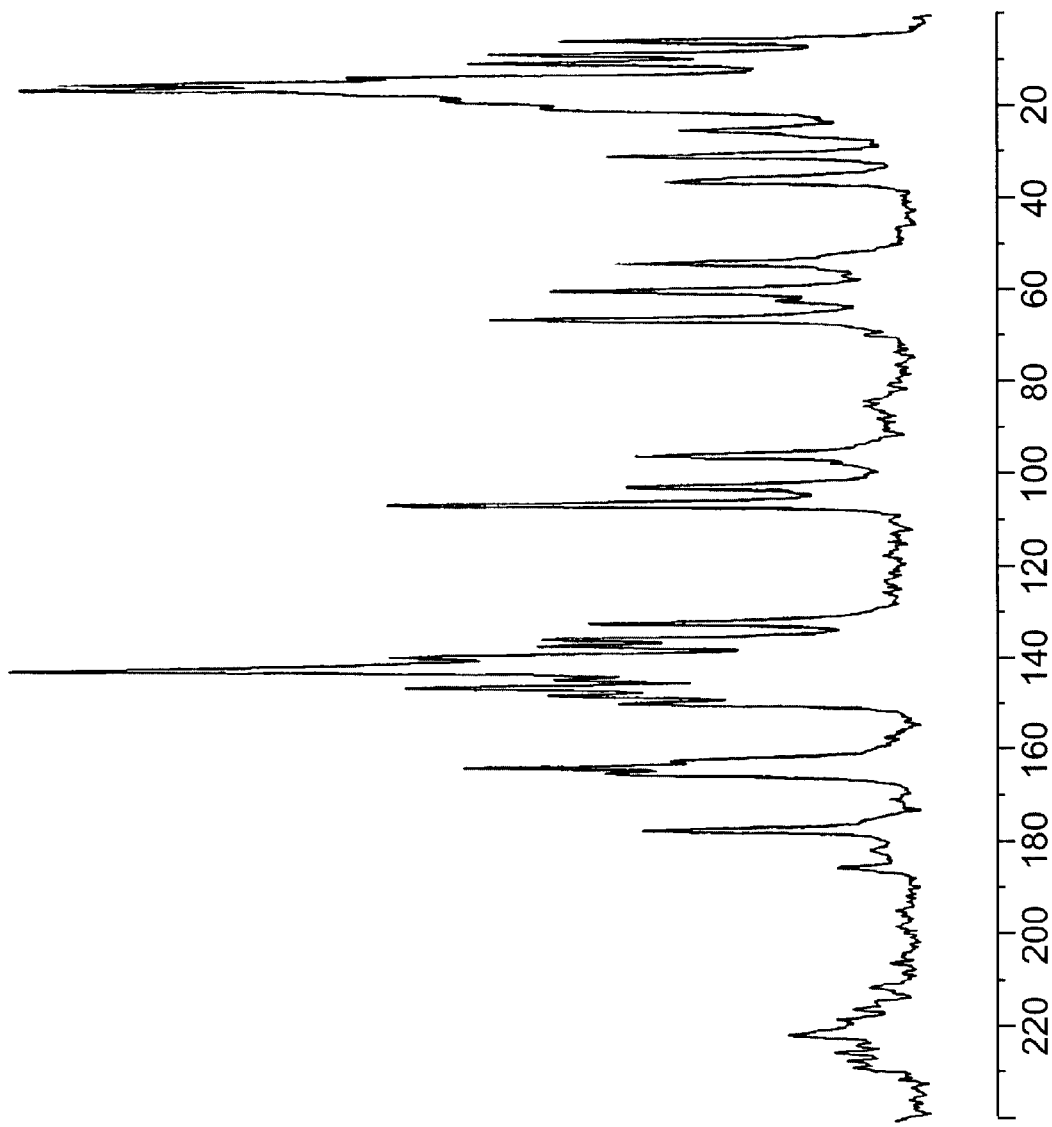
FIG. 10 illustrates the Solid State NMR Spectrum of the N,N-Dimethylformamide Solvate of SnET2.

The dimethylformamide, or DMF, solvate of SnET2 may be characterized by the fact that it crystallizes with approximately one mole of dimethylformamide and by its X-ray diffraction pattern and solid state NMR spectrum as shown in FIGS. 9 and 10, respectively. Referring to FIG. 9, the X-ray diffraction pattern was measured using a Siemens D-500 Diffraktometer-Kristalloflex with an IBM-compatible interface, software=DIFFRAC AT (SOCABIM 1986, 1992). CuK$\alpha$ radiation (20 mA, 40 kV, $\lambda$=1.5406 Å) (Slits I and II at 1°) was electronically filtered by the Kevex Psi Peltier Cooled Silicon [Si(Li)] Detector (Slits: III at 1°, IV at 0.15°). Referring to FIG. 10, the solid state NMR spectrum was measured on a Bruker AC 250 mHz spectrometer using high-power proton decoupling and cross-polarization (CP) with magic-angle spinning (MAS) at approximately 5 KHz. The magic-angle was adjusted using the spinning sidebands of the $^{79}$Br signal of solid KBr according to the method of Frye and Maciel (Frye, J. S. and Maciel, G. E. *J. Magn. Reson.* (1982) 48, 125–31). Approximately 250–300 mg of sample was packed into a suitable rotor. Chemical shifts are relative to an appropriate external standard, which is tetrakis (trimethylsilyl)silane (methyl signal at 3.50 ppm).

Table 9 lists the 2θ values, "d-spacings", and relative intensities of the major lines in the diffraction pattern of the dimethylformamide solvate of SnET2.

TABLE 9

Intensities and peak locations of all major diffraction lines in dimethylformamide solvate of SnET2.

| 2θ | d | Rel. I |
|---|---|---|
| 7.4 | 12.0 | 100 |
| 9.0 | 9.8 | 46 |
| 9.8 | 9.0 | 12 |
| 11.7 | 7.6 | 66 |
| 14.7 | 6.0 | 13 |
| 15.5 | 5.7 | 16 |
| 19.1 | 4.6 | 12 |
| 20.1 | 4.4 | 19 |
| 21.2 | 4.2 | 12 |
| 22.2 | 4.0 | 10 |
| 23.5 | 3.8 | 8 |
| 27.2 | 3.3 | 8 |
| 28.8 | 3.1 | 13 |

TABLE 10

Solid state NMR chemical shifts of dimethylformamide solvate of SnET2. The column labeled delta reports the chemical shifts relative to the lowest field signal.

| Chemical Shift (ppm) | Delta (ppm) |
|---|---|
| 176.9 | 171.5 |
| 164.5 | 159.1 |
| 163.2 | 157.8 |
| 161.9 | 156.5 |
| 149.1 | 143.7 |
| 147.4 | 142 |
| 145.5 | 140.1 |
| 143.8 | 138.4 |
| 141.6 | 136.2 |
| 138.8 | 133.4 |
| 136.4 | 131 |
| 134.9 | 129.5 |
| 131.5 | 126.1 |
| 105.7 | 100.3 |
| 102.1 | 96.7 |
| 95.4 | 90 |
| 65.8 | 60.4 |
| 61.9 | 56.5 |
| 59.8 | 54.4 |
| 53.7 | 48.3 |
| 36.2 | 30.8 |
| 30.8 | 25.4 |
| 24.7 | 19.3 |
| 15.7 | 10.3 |
| 14.4 | 9 |
| 10.1 | 4.7 |
| 8.2 | 2.8 |
| 5.4 | 0 |

The effects of pressure on polymorphic forms varies based on the compound. Common processing operations, such as milling, can cause solid form transformations. Sometimes grinding can be used to generate amorphous material, as in the case of permethylated β-cyclodextrin [I. Tsukushi, O. Yamamuro, and H. Suga, Heat capacities and glass transitions of ground amorphous solid and liquid-quenched glass of tri-O-methyl-β-cyclodextrin, *Journal of Non-Crystalline Solids* 175:187 (1994)] and ursodeoxycholic acid [E. Yonemochi, Y. Inoue, G. Buckton, A. Moffat, T. Oguchi, and K. Yamamoto, Differences in Crystallization Behavior Between Quenched and Ground Amorphous Ursodeoxycholic Acid, *Pharm. Res.* 16:835 (1999)]. It is also possible to bring about crystalline form changes by grinding, including generation of a metastable form from a stable form in certain cases. In an interesting example, grinding of the antineoplastic cyclophosphamide monohydrate results in dehydration. Loss of the water occurs without a significant change in the crystal lattice, affording a metastable, anhydrous crystal form which undergoes a solid state transformation to a more stable polymorph [J. Ketolainen, A. Poso, V. Viitasaari, J. Gynther, J. Pirttimäki, E. Laine, and P. Paronen, Changes in Solid-State Structure of Cyclophosphamide Monohydrate Induced by Mechanical Treatment and Storage, *Pharm. Res.* 12:299 (1995)].

Figure 11:
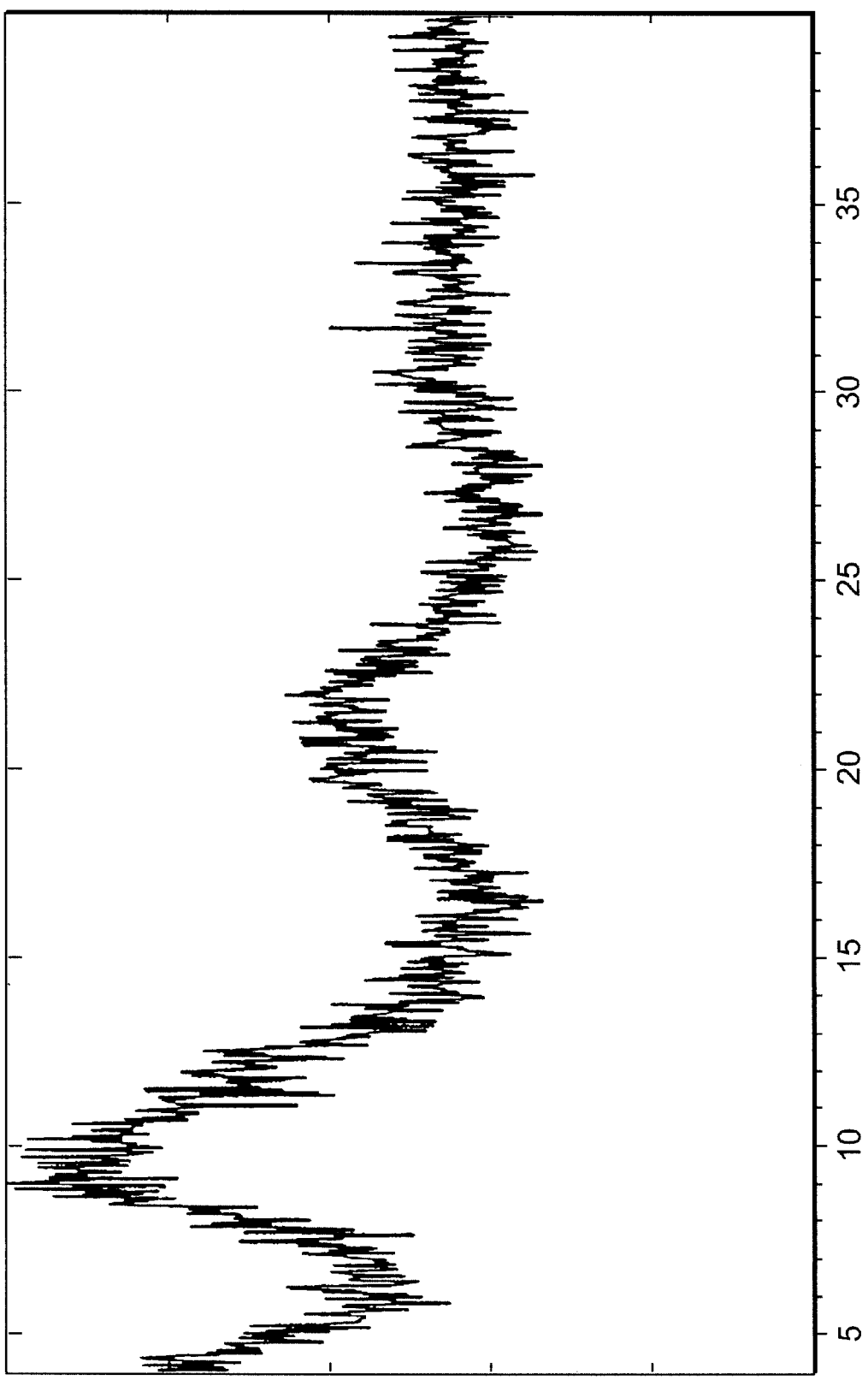
FIG. 11 illustrates the X-Ray Diffraction Pattern of the Amorphous Form of SnET2.

The amorphous form of SnET2 can be formed readily upon grinding the crystalline form and may be characterized by its X-ray diffraction pattern as shown in FIG. 11. Referring to FIG. 11, the X-ray diffraction pattern was measured using a Siemens D-500 Diffraktometer-Kristalloflex with an IBM-compatible interface, software=DIFFRAC AT (SOCABIM 1986, 1992). CuKα radiation (20 mA, 40 kV, λ=1.5406 Å) (Slits I and II at 1°) was electronically filtered by the Kevex Psi Peltier Cooled Silicon [Si(Li)] Detector (Slits: III at 1°, IV at 0.15°).

The diffraction pattern for the amorphous form of SnET2 has two broad peaks centered at approximately 10 degrees and 21 degrees 2θ.

Crystalline Forms I and II, disordered Form II and the amorphous form of SnET2 may be formulated for administration in any convenient way and the invention includes within its scope pharmaceutical compositions comprising crystalline Form I or Form II, disordered Form II, the amorphous form of SnET2 or mixtures thereof adapted for use in human or veterinary medicine. Such compositions may be presented for use in a conventional manner with the aid of a pharmaceutically acceptable carrier or excipient and may also contain, if required, other active ingredients. Thus, SnET2 according to the invention may be formulated for oral, buccal, topical, parenteral or rectal administration.

The solvates of SnET2 after desolvation (removal of the solvent) may be formulated for administration in any convenient way and the invention includes within its scope pharmaceutical compositions including desolvated solvates or mixtures thereof adapted for use in human or veterinary medicine. Such compositions may be presented for use in a conventional manner with the aid of a pharmaceutically acceptable carrier or excipient and may also contain, if required, other active ingredients. Thus, SnET2 according to the invention may be formulated for oral, buccal, topical, parenteral or rectal administration.

For oral administration the pharmaceutical composition may take the form of, for example, tablets, capsules, powders, solutions, syrups or suspensions prepared by conventional means with acceptable excipients. For buccal administration the compositions may take the form of tablets or lozenges formulated in a conventional manner.

The solid forms of SnET2 may be formulated for parenteral administration by bolus injection or continuous infusion. Formulations for injection may be presented in unit dosage form in ampoules, or in multidose containers, with an added preservative. The composition may take such forms as suspensions, solutions or emulsions in oily or aqueous vehicles, and may contain formulatory agents such as suspending, stabilizing and/or dispersing agents. Alternatively, the active ingredient may be in powder form for reconstitution with a suitable vehicle before use.

The solid forms may also be formulated in rectal compositions such as suppositories or retention enemas, e.g., containing conventional suppository bases such as cocoa butter or other glycerides.

For topical application, the solid forms may be formulated as ointments, creams, gels, lotions, powders or sprays in a conventional manner.

The present invention also provides a process for the preparation of the solid forms of SnET2 which comprises precipitating or crystallizing SnET2 from a solution thereof in a solvent under conditions which yield the solid forms or grinding or processing the solid forms in such a way that it produces the amorphous form. The precise conditions under which each form is produced may be empirically determined and it is only possible to give a number of methods which have been found to be suitable in practice.

Crystalline Form I of SnET2 may be prepared by crystallization under controlled conditions. For example, it can be prepared from either crystalline Form I or Form II by recrystallization from dichloroethane, chloroform, 1,1,2-trichloroethane, or tetrahydrofuran, or mixtures of one of these with acetone, acetonitrile, ethyl acetate, hexane, or acetic acid, or dichloromethane/acetic acid mixtures.

Crystalline Form II of SnET2 may be prepared by crystallization under controlled conditions. For example, it can be prepared from either crystalline Form I or Form II by recrystallization from dichloromethane or dichloromethane/acetone mixtures, or by slurrying crystalline Form I or Form II in the same solvents.

Disordered Form II SnET2 may be prepared by crystallization under controlled conditions. For example, it can be prepared from crystalline Form I by recrystallization from dichloromethane/acetone mixtures, or by slurrying crystalline Form I in the same solvents.

The amorphous form of SnET2 can be prepared by any method that yields the amorphous form, such as grinding. For example, grinding of either crystalline Form I or Form II in a Wig-L-Bug® amalgamator for 60 minutes affords amorphous SnET2. The amorphous form of SnET2 may also be prepared by, for example, freeze drying, quench cooling, rapid evaporation of, or rapid cooling of, a solution of SnET2 in an appropriate solvent.

By way of example, the 1,2-dichloroethane solvate of SnET2 may be prepared by crystallization under controlled conditions. In particular, it can be prepared from any solid form by recrystallization from 1,2-dichloroethane.

The dimethylformamide solvate of SnET2 may be prepared by, for example, crystallization under controlled conditions. In particular, it can be prepared from any solid form by recrystallization from dimethylformamide.

In order to be more fully understood, the following examples are given by way of illustration only. All temperatures are in ° C.

| EXAMPLES | |
|---|---|
| Example 1 | Preparation of crystalline Form I |
| Example 2 | Preparation of crystalline Form I from a different solvent |
| Example 3 | Preparation of crystalline Form II |
| Example 4 | Preparation of crystalline Form II from a different solvent |

-continued

| EXAMPLES | |
|---|---|
| Example 5 | Preparation of crystalline Form II by slurry conversion |
| Example 6 | Preparation of disordered Form II |
| Example 7 | Preparation of the DCE solvate |
| Example 8 | Preparation of the DMF solvate |
| Example 9 | Preparation of the DMF solvate from solvent mixtures |
| Example 10 | Preparation of amorphous form |
| Example 11 | Enhanced stability of crystalline form |

EXAMPLE 1

Preparation of SnET2 Crystalline Form I from Dichloromethane/Acetic Acid

Under subdued lighting, approximately 155 g of SnET2 were dissolved in 5300 mL of dichloromethane. The dichloromethane was reduced to approximately 3500 mL under vacuum (40° C., 660 mbar) and the resulting slurry was treated portion-wise with 1250 mL of acetic acid as the dichloromethane was removed by evaporation over 1 hour 30 minutes (45° C., 600 mbar to 55° C., 380 mbar). The resulting solid was collected by filtration, rinsed with 1000 mL of acetic acid, followed by 500 mL of acetone, and dried at 54 to 60° C., 28–30" Hg. The XRPD analysis indicated crystalline Form I.

EXAMPLE 2

Preparation of SnET2 Crystalline Form I from Different Solvents

Crystalline Form I was generated from the solvents listed below in Table 11 by evaporation, cooling or antisolvent treatment of SnET2 in the said solvent. Under subdued lighting, a weighed sample of SnET2 (usually 60–100 mg) was treated with aliquots of a specific solvent (usually either 100 μL or 1 mL) until the SnET2 dissolved. The solution was then filtered and the solid was crystallized from the filtrate by one of four methods; slow evaporation, fast evaporation, slow cool or precipitation. For the fast evaporation method, the filtrate was evaporated in an open vial at ambient conditions. For the slow evaporation method, the filtrate was evaporated in a vial covered with a perforated cover at ambient conditions. For the slow cool method, the solution was heated during dissolution and filtration, and then the filtrate was cooled to 3° C. or −20° C. For the precipitation method, the filtrate was treated with the antisolvent at ambient temperature until precipitation occurred. The resulting solid was collected and found, by XRPD analysis, to be crystalline Form I.

TABLE 11

| Solvent | Crystallization Method |
|---|---|
| Trichloroethane | Fast evaporation |
|  | Slow evaporation |
| Tetrahydrofuran | Fast evaporation |
|  | Slow cool |
| Acetone | Fast evaporation |
|  | Slow cool |
| Dichloromethane/acetone | Precipitation |
| Dichloromethane/acetonitrile | Precipitation |
| Dichloromethane/ethyl acetate | Precipitation |
| Dichloromethane/acetic acid | Precipitation |
| Dichloromethane/hexane | Precipitation |

TABLE 11-continued

| Solvent | Crystallization Method |
|---|---|
| Chloroform/acetone | Precipitation |
| Chloroform/acetonitrile | Precipitation |
| Chloroform/ethyl acetate | Precipitation |
| Chloroform/acetic acid | Precipitation |
| Chloroform/hexane | Precipitation |
| Dichloroethane/acetone | Precipitation |
| Dichloroethane/acetonitrile | Precipitation |
| Dichloroethane/ethyl acetate | Precipitation |
| Dichloroethane/acetic acid | Precipitation |
| Dichloroethane/hexane | Precipitation |

EXAMPLE 3

Preparation of SnET2 Crystalline Form II from Dichloromethane/Acetic Acid Followed by Dichloromethane/Acetone Under subdued lighting, approximately 160 g of SnET2 were dissolved in 8300 mL of dichloromethane. The dichloromethane was reduced to approximately 3500 mL under vacuum (36–38° C., 615–600 mbar) and the resulting slurry was treated portion-wise with 1250 mL of acetic acid as the dichloromethane was removed by evaporation over 1 hour 21 minutes (40° C., 600 mbar to 54° C., 380 mbar). The resulting solid was collected by filtration, rinsed with 1000 mL of acetic acid, followed by 500 mL of acetone, and dried at 50 to 56° C., 28–30" Hg. Then the dry solid material (160 g) was mixed with 4500 mL of dichloromethane and warmed at 42–44° C. for 31 minutes. The solution was treated with 2640 mL of acetone as the dichloromethane was removed by evaporation over 2 hours and 58 minutes (42° C., 750 mbar to 50° C., 750 mbar). The resulting solid was collected by filtration, rinsed with 1060 mL of acetone and dried at 54–56° C., 30" Hg. The XRPD analysis indicated crystalline Form II.

EXAMPLE 4

Preparation of SnET2 Crystalline Form II from Different Solvents

Crystalline Form II was generated from the solvents listed below in Table 12 by evaporation or cooling of SnET2 in the said solvent. Under subdued lighting, a weighed sample of SnET2 (usually 60–100 mg) was treated with aliquots of a specific solvent (usually either 100 μL or 1 mL) until the SnET2 dissolved. The solution was then filtered and the solid was crystallized from the filtrate by one of three methods; slow evaporation, fast evaporation or slow cool. For the fast evaporation method, the filtrate was evaporated in an open vial at ambient conditions. For the slow evaporation method, the filtrate was evaporated in a vial covered with a perforated cover at ambient conditions. For the slow cool method, the solution was heated during dissolution and filtration, and then the filtrate was cooled to 3° C. or –20° C. The resulting solid was collected and found, by XRPD analysis, to be crystalline Form II.

TABLE 12

| Solvent | Crystallization Method |
|---|---|
| Methanol | Fast evaporation |
|  | Slow evaporation |

TABLE 12-continued

| Solvent | Crystallization Method |
|---|---|
| Dichloromethane | Slow evaporation |
| Acetonitrile | Fast evaporation |
|  | Slow cool |

EXAMPLE 5

Preparation of SnET2 Crystalline Form II by Slurry Interconversion

Under subdued lighting, a slurry containing a 1:1 mixture of SnET2 crystalline Form I and SnET2 crystalline Form II (100–200 mg each) in 1–3 mL of a solvent, listed in Table 13 below, was agitated in a tightly-capped tube at ambient temperature or at 50° C. The undissolved solid was collected by filtration and found, by XRPD analysis, to be crystalline Form II.

TABLE 13

| Solvents (amount mL) | Temperature |
|---|---|
| Dichloromethane (3) | ambient |
| Acetone (3) | ambient |
| Dichloromethane/acetone (2:1) | ambient |
| Dichloromethane (3) | 50° C. |
| Acetone (3) | 50° C. |
| Dichloromethane/acetone (2:1) | 50° C. |

EXAMPLE 6

Preparation of SnET2 Disordered Form II from Dichloromethane/Acetic Acid followed by Dichloromethane/Acetone Under subdued lighting, approximately 160 g of SnET2 were dissolved in 5300 mL of dichloromethane. The dichloromethane was reduced to approximately 3500 mL under vacuum (31–39° C., 700–660 mbar) and the resulting slurry was treated portion-wise with 1250 mL of acetic acid as the dichloromethane was removed by evaporation over 1 hour 46 minutes (40° C., 660 mbar to 55° C., 380 mbar). The resulting solid was collected by filtration, rinsed with 1000 mL of acetic acid, followed by 500 mL of acetone, and dried at 49 to 59° C., 28–30" Hg. Then the dry solid material (157 g) was mixed with 4500 mL of dichloromethane and warmed at 37–42° C. for 30 minutes. The solution was treated with 2590 mL of acetone as the dichloromethane was removed by evaporation over 1 hour and 55 minutes (42° C., 700 mbar to 50° C., 670 mbar). The resulting solid was collected by filtration, rinsed with 1040 mL of acetone and dried at 54–56° C., 30" Hg. The XRPD analysis indicated disordered Form II.

EXAMPLE 7

Preparation of a 1,2-Dichloroethane Solvate of SnET2

Under subdued lighting, 3 mL of 1,2-dichloroethane (DCE) were added to 100 mg of SnET2. The resulting mixture was filtered through a glass wool plug and the filtrate was left in an open vial in the dark. When all of the DCE had evaporated, the solid residue was isolated and found to be the DCE solvate by elemental analysis and by its X-ray diffraction pattern and solid state NMR spectrum.

EXAMPLE 8

Preparation of an N,N-dimethylformamide Solvate of SnET2

Under subdued lighting, 40 mL of N,N-dimethylformamide were added to 1 g of SnET2. The resulting mixture was gravity filtered through hardened filter paper and the filtrate was left in an open vial in the dark. When most of the DMF had evaporated, the residue was placed under vacuum at ambient temperature overnight. The solid residue was shown to be the DMF solvate by its elemental analysis and by its X-ray diffraction pattern and solid state NMR spectrum.

EXAMPLE 9

Preparation of an N,N-dimethylformamide Solvate of SnET2 from Solvent Mixtures The N,N-dimethylformamide solvate of SnET2 was generated from the solvents listed below in Table 14 by treating a solution of SnET2 in the said solvent with N,N-dimethylformamide. Under subdued lighting, a weighed sample of SnET2 (usually 60–100 mg) was treated with aliquots of a specific solvent (usually either 100 µL or 1 mL) until the SnET2 dissolved. The solution was then filtered and the filtrate was treated with N,N-dimethylformamide at ambient temperature until precipitation occurred. The resulting solid was collected and found, by XRPD analysis, to be the N,N-dimethylformamide solvate of SnET2.

TABLE 14

| Solvents | Crystallization Method |
| --- | --- |
| Chloroform/N,N-dimethylformamide | precipitation |
| Dichloroethane/N,N-dimethylformamide | precipitation |

EXAMPLE 10

Preparation of Amorphous SnET2

Under subdued lighting, a 20×50 mm stainless-steel canister was charged with a stainless-steel ball and SnET2 to about ¾ full. This was agitated in a Wig-L-Bug® amalgamator. Periodically, material was removed and analyzed by XRPD. After one hour of grinding the SnET2 was found to be amorphous.

EXAMPLE 11

Enhanced Stability of Crystalline Form

Comparative stability studies were performed on crystalline Form I, crystalline Form II, disordered Form II and the amorphous form. Light stability studies were carried out in a closed, black 30×16×12 inch cabinet containing two 24-inch, 20-watt fluorescent bulbs as the light source. The samples were placed approximately 10 inches from the bulbs. Each sample consisted of approximately 30-mg of SnET2 in a 1-dram vial. Samples were removed at the time intervals indicated in Table 11, analyzed by XRPD and HPLC. HPLC data analysis indicated that the photoproduct was produced more rapidly in the amorphous form than any other form when exposed to visible light.

TABLE 15

Stability of SnET2 Solid Forms Under Visible Light Irradiation

| Starting Form | Time (days) | XRPD Result | Impurity Levels by HPLC | | |
| --- | --- | --- | --- | --- | --- |
| | | | Peak 1[a] | Peak 2 | Peak 3 |
| Disordered Form II | 0 | Disordered FII | 0.65 | 0.10 | 0.19 |
| | 2 | Disordered FII | 1.24 | 0.13 | 0.19 |
| | 4 | Disordered FII | 1.98 | 0.09 | 0.27 |
| | 6 | Disordered FII | 2.51 | 0.11 | 0.28 |
| | 8 | Disordered FII | 1.77 | 0.12 | 0.28 |
| | 19 | Disordered FII | 3.54 | 0.06 | 0.32 |
| | 29 | Disordered FII | 4.92 | 0.10 | 0.51 |
| Crystalline Form II | 0 | Crystalline Form II | 0.00 | 0.23 | 0.00 |
| | 2 | Crystalline Form II | 0.44 | 0.23 | 0.04 |
| | 4 | Crystalline Form II | 0.56 | 0.24 | 0.09 |
| | 6 | Crystaliine Form II | 0.82 | 0.21 | 0.10 |
| | 8 | Crystalline Form II | 0.96 | 0.21 | 0.15 |
| | 19 | Crystalline Form II | 1.12 | 0.18 | 0.14 |
| | 29 | Crystalline Form II | 1.68 | 0.17 | 0.11 |
| Crystalline Form I | 0 | Crystalline Form I | 0.20 | 0.15 | 0.0 |
| | 2 | Crystalline Form I | 0.89 | 0.16 | 0.0 |
| | 4 | Crystalline Formn I | 9.61 | 0.84 | 0.0 |
| | 6 | Crystalline Form I | 2.16 | 0.14 | 0.09 |
| | 8 | Crystalline Form I | 1.87 | 0.15 | 0.13 |
| | 19 | Crystalline Form I | 2.39 | 0.34 | 0.17 |
| | 29 | Crystalline Form I | 4.47 | 0.11 | 0.21 |
| Amorphous | 0 | Amorphous | 1.62 | 0.70 | 0.00 |
| | 2 | Amorphous | 6.60 | 0.71 | 0.03 |
| | 4 | Amorphous | 9.78 | 0.73 | 0.15 |
| | 6 | Amorphous | 1.84 | 0.11 | 0.23 |
| | 8 | Amorphous | 12.66 | 0.70 | 0.27 |
| | 19 | Amorphous | 14.13 | 0.73 | 0.38 |
| | 29 | Amorphous | 18.72 | 0.76 | 0.38 |

[a]peak 1 is the photooxidized product

It will be apparent to those skilled in the art that various modifications and variations can be made in the present invention without departing from the spirit or scope of the invention. Thus, it is intended that the present description cover the modifications and variations of this invention provided that they come within the scope of the appended claims and their equivalents.

We claim:

1. Crystalline Form I of tin ethyl etiopurpurin having an X-ray diffraction pattern with a powder diffraction line at 6.5 degrees 2θ measured with CuK$_\alpha$ radiation.

2. The crystalline Form I of tin ethyl etiopurpurin of claim 1 having additional powder diffraction lines at 12.9 and 14 degrees 2θ measured with CuK$_\alpha$ radiation.

3. The crystalline Form I of tin ethyl etiopurpurin of claim 1 having an X-ray diffraction pattern with the following powder diffraction lines measured with CuK$_\alpha$ radiation:

| 2θ | d | Rel. I (>9%) |
|---|---|---|
| 6.5 | 13.5 | 52 |
| 8.6 | 10.3 | 100 |
| 12.9 | 6.8 | 17 |
| 14.0 | 6.3 | 15 |
| 15.2 | 5.8 | 12 |
| 15.7 | 5.6 | 24 |
| 16.9 | 5.2 | 10 |
| 18.7 | 4.8 | 19 |
| 19.5 | 4.6 | 12 |
| 23.0 | 3.9 | 10 |
| 23.4 | 3.8 | 29 |
| 26.3 | 3.4 | 13 |
| 28.6 | 3.1 | 14 |
| 30.0 | 3.0 | 10 |
| 37.6 | 2.4 | 9. |

4. The crystalline Form I of tin ethyl etiopurpurin of claim 3 having substantially the X-ray diffraction pattern of FIG. 1.

5. Crystalline Form I of tin ethyl etiopurpurin having a solid state NMR resonance at 25.6 ppm.

6. The crystalline Form I of tin ethyl etiopurpurin of claim 5 further having a solid state NMR resonance at 165.6 ppm.

7. Crystalline Form I of tin ethyl etiopurpurin having a solid state NMR delta of 16.2 ppm.

8. The crystalline Form I of tin ethyl etiopurpurin of claim 7 further having a solid state NMR delta of 156.2 ppm.

9. The crystalline Form I of tin ethyl etiopurpurin of claim 5 having a solid state NMR spectrum with the following chemical shifts:

| Chemical Shift (ppm) | Delta (ppm) |
|---|---|
| 177.5 | 168.1 |
| 165.6 | 156.2 |
| 163.8 | 154.4 |
| 149.8 | 140.4 |
| 145.5 | 136.1 |
| 143.8 | 134.4 |
| 140.4 | 131 |
| 134.4 | 125 |
| 130.1 | 120.7 |
| 104 | 94.6 |
| 97 | 87.6 |
| 67.1 | 57.7 |
| 58.9 | 49.5 |
| 54.2 | 44.8 |
| 25.6 | 16.2 |
| 16.1 | 6.7 |
| 12.8 | 3.4 |
| 9.4 | 0. |

10. The crystalline Form I of tin ethyl etiopurpurin of claim 9 having substantially the solid state NMR spectrum of FIG. 2.

11. Crystalline Form II of tin ethyl etiopurpurin having an X-ray diffraction pattern with a powder diffraction line at 12.2 degrees 2θ measured with $CuK_\alpha$ radiation.

12. The crystalline Form II of tin ethyl etiopurpurin of claim 11 having additional powder diffraction lines at 12.5 and 8.4 degrees 2θ measured with $CuK_\alpha$ radiation.

13. The crystalline Form II of tin ethyl etiopurpurin of claim 11 having the following powder diffraction lines measured with $CuK_\alpha$ radiation:

| 2θ | d | Rel. I (>10%) | PWHH (° 2θ) |
|---|---|---|---|
| 8.4 | 10.6 | 100 | 0.23 |
| 8.9 | 10.0 | 51 | 0.22 |
| 9.5 | 9.4 | 31 | 0.23 |
| 12.2 | 7.3 | 42 | 0.21 |
| 12.5 | 7.1 | 29 | 0.28 |
| 16.7 | 5.3 | 12 | 0.22 |
| 17.8 | 5.0 | 12 | 0.22 |
| 19.5 | 4.6 | 24 | 0.30 |
| 21.8 | 4.1 | 39 | 0.28 |
| 27.9 | 3.2 | 11 | 0.22 |
| 28.2 | 3.2 | 20 | 0.25 |
| 30.6 | 2.9 | 13 | 0.29 |
| 33.2 | 2.7 | 14 | 0.29 |
| 34.5 | 2.6 | 11 | 0.31 |
| 39.5 | 2.3 | 12 | 0.33. |

14. The crystalline Form II of tin ethyl etiopurpurin of claim 11 having substantially the X-ray diffraction pattern of FIG. 3.

15. Form II of tin ethyl etiopurpurin having a solid state NMR resonance at 29.8–29.9 ppm.

16. The Form II of tin ethyl etiopurpurin of claim 15 further having a solid state NMR resonance at 163.4–163.6 ppm.

17. Form II of tin ethyl etiopurpurin having a solid state NMR delta of 21.1–21.4 ppm.

18. The Form II of tin ethyl etiopurpurin of claim 17 further having a solid state NMR delta of 154.9 ppm.

19. The Form II of tin ethyl etiopurpurin of claim 15 having a solid state NMR spectrum with the following chemical shifts:

| Chemical Shift (ppm) | Delta (ppm) |
|---|---|
| 178.7 | 170.0–170.2 |
| 166.8–168.0 | 158.1–159.3 |
| 163.4–163.6 | 154.9 |
| 148.5–148.6 | 139.8–140.1 |
| 146.3 | 137.6–137.8 |
| 144.2–144.3 | 135.6–135.7 |
| 140.1–140.2 | 131.4–131.7 |
| 136.9–137.1 | 128.4 |
| 135.0–135.2 | 126.5 |
| 130.3–130.4 | 121.7–121.8 |
| 105.6–105.9 | 97.1–97.2 |
| 102.8–103.0 | 94.3 |
| 101.6 | 92.9–93.1 |
| 95.1–95.2 | 86.4–86.7 |
| 65.7–66.3 | 57.2–57.6 |
| 60.4–60.6 | 51.9 |
| 53.0–53.3 | 44.5–44.6 |
| 29.8–29.9 | 21.1–21.4 |
| 19.1–19.4 | 10.6–10.7 |
| 15.1 | 6.4–6.6 |
| 9.9–10.1 | 1.4 |
| 8.5–8.7 | 0. |

20. Crystalline Form II of tin ethyl etiopurpurin having substantially the solid state NMR spectrum of FIG. 4.

21. Disordered Form II of tin ethyl etiopurpurin having substantially the solid state NMR spectrum of FIG. 6.

22. Disordered Form II of tin ethyl etiopurpurin having an X-ray diffraction pattern with a powder diffraction line with a maxima at 11.5–13.5 degrees 2θ measured with $CuK_\alpha$ radiation.

23. The disordered Form II of tin ethyl etiopurpurin of claim 22 having a further powder diffraction line with maxima at 7.5–8.5 degrees 2θ measured with CuK$_α$ radiation.

24. The disordered Form II of tin ethyl etiopurpurin of claim 22 having the following powder diffraction lines measured with CuK$_α$ radiation:

| 2θ Broad peak maxima centered between: | d | Rel. I | PWHH (° 2θ) |
|---|---|---|---|
| 7.5–8.5 | 10.6 | 100 | 0.39 |
| 8.5–10.5 | 9.8 | 88 | 0.64 |
| 11.5–13.5 | 7.2 | 85 | 0.65 |
| 15.0–16.0 | 5.7 | 22 | 0.41 |
| 17.0–19.0 | 5.0 | 30 | 0.63 |
| 19.0–20.5 | 4.4 | 32 | 0.63 |
| 20.5–21.5 | 4.2 | 33 | 0.89 |
| 21.5–23.0 | 4.0 | 33 | 0.80 |
| 23.0–24.5 | 3.7 | 24 | 0.77 |
| 24.5–26.0 | 3.5 | 23 | 0.76 |
| 27.0–28.0 | 3.2 | 26 | 0.73 |
| 28.0–29.5 | 3.1 | 32 | 0.80 |
| 29.5–31.0 | 2.9 | 25 | 1.28 |
| 31.0–32.5 | 2.8 | 22 | 0.66. |

25. The disordered Form II of tin ethyl etiopurpurin of claim 22 having substantially the X-ray diffraction pattern of FIG. 5.

26. The 1,2-dichloroethane solvate of tin ethyl etiopurpurin having an X-ray diffraction pattern with a powder diffraction line at 10.0 degrees 2θ measured with CuK$_α$ radiation.

27. The 1,2-dichloroethane solvate of tin ethyl etiopurpurin of claim 26 having further powder diffraction lines at 6.6 and 21.4 degrees 2θ measured with CuK$_α$ radiation.

28. The 1,2-dichloroethane solvate of tin ethyl etiopurpurin of claim 26 having the following powder diffraction lines measured with CuK$_α$ radiation:

| 2θ | d | Rel. I |
|---|---|---|
| 6.6 | 13.4 | 100 |
| 7.5 | 11.8 | 6 |
| 8.4 | 10.6 | 14 |
| 10.0 | 8.9 | 36 |
| 10.5 | 8.4 | 9 |
| 13.1 | 6.8 | 9 |
| 13.9 | 6.3 | 11 |
| 15.1 | 5.9 | 18 |
| 15.5 | 5.7 | 20 |
| 16.2 | 5.5 | 12 |
| 19.7 | 4.5 | 9 |
| 20.9 | 4.2 | 12 |
| 21.4 | 4.1 | 25 |
| 24.4 | 3.6 | 5 |
| 26.0 | 3.4 | 11 |
| 28.4 | 3.1 | 4 |
| 29.1 | 3.1 | 5 |
| 29.7 | 3.0 | 7 |
| 34.5 | 2.6 | 6. |

29. The 1,2-dichloroethane solvate of tin ethyl etiopurpurin of claim 26 having substantially the X-ray diffraction pattern of FIG. 7.

30. The 1,2-dichloroethane solvate of tin ethyl etiopurpurin having a solid state NMR resonance at 19.7 ppm.

31. The 1,2-dichloroethane solvate of tin ethyl etiopurpurin of claim 30 having a further solid state NMR resonance at 164.6 ppm.

32. The 1,2-dichloroethane solvate of tin ethyl etiopurpurin of claim 30 having a solid state NMR delta of 10.7 ppm.

33. The 1,2-dichloroethane solvate of tin ethyl etiopurpurin of claim 32 having a further solid state NMR delta of 155.6 ppm.

34. The 1,2-dichloroethane solvate of tin ethyl etiopurpurin of claim 30 having a solid state NMR spectrum with the following chemical shifts:

| Chemical Shift (ppm) | Delta (ppm) |
|---|---|
| 176.8 | 167.8 |
| 164.6 | 155.6 |
| 149.4 | 140.4 |
| 145.8 | 136.8 |
| 143.9 | 134.9 |
| 140.6 | 131.6 |
| 134.8 | 125.8 |
| 133.9 | 124.9 |
| 129.9 | 120.9 |
| 104.6 | 95.6 |
| 97.1 | 88.1 |
| 66.5 | 57.5 |
| 59.6 | 50.6 |
| 53.9 | 44.9 |
| 45.7 | 36.7 |
| 42.7 | 33.7 |
| 26 | 17 |
| 19.7 | 10.7 |
| 16.9 | 7.9 |
| 12.8 | 3.8 |
| 9 | 0. |

35. The 1,2-dichloroethane solvate of tin ethyl etiopurpurin of claim 34 having substantially the solid state NMR spectrum of FIG. 8.

36. The N,N-dimethylformamide solvate of tin ethyl etiopurpurin having an X-ray diffraction pattern with a powder diffraction line at 7.4 degrees 2θ measured with CuK$_α$ radiation.

37. The N,N-dimethylformamide solvate of tin ethyl etiopurpurin of claim 36 having further powder diffraction lines at 9.0 and 11.7 degrees 2θ measured with CuK$_{60}$ radiation.

38. The N,N-dimethylformamide solvate of tin ethyl etiopurpurin of claim 36 having the following powder diffraction lines measured with CuK$_α$ radiation:

| 2θ | d | Rel. I |
|---|---|---|
| 7.4 | 12.0 | 100 |
| 9.0 | 9.8 | 46 |
| 9.8 | 9.0 | 12 |
| 11.7 | 7.6 | 66 |
| 14.7 | 6.0 | 13 |
| 15.5 | 5.7 | 16 |
| 19.1 | 4.6 | 12 |
| 20.1 | 4.4 | 19 |
| 21.2 | 4.2 | 12 |
| 22.2 | 4.0 | 10 |
| 23.5 | 3.8 | 8 |
| 27.2 | 3.3 | 8 |
| 28.8 | 3.1 | 13. |

39. The N,N-dimethylformamide solvate of tin ethyl etiopurpurin of claim 37 having substantially the X-ray diffraction pattern of FIG. 9.

40. The N,N-dimethylformamide solvate of tin ethyl etiopurpurin having a solid state NMR resonance at 8.2 ppm.

41. The N,N-dimethylformamide solvate of tin ethyl etiopurpurin of claim 40 having a further solid state NMR resonance at 102.9 ppm.

42. The N,N-dimethylformamide solvate of tin ethyl etiopurpurin having a solid state NMR delta of 2.8 ppm.

43. The N,N-dimethylformamide solvate of tin ethyl etiopurpurin of claim 42 having a further solid state NMR delta of 100.3 ppm.

44. The N,N-dimethylformamide solvate of tin ethyl etiopurpurin of claim 40 having a solid state NMR spectrum with the following chemical shifts:

| Chemical Shift (ppm) | Delta (ppm) |
|---|---|
| 176.9 | 171.5 |
| 164.5 | 159.1 |
| 163.2 | 157.8 |
| 161.9 | 156.5 |
| 149.1 | 143.7 |
| 147.4 | 142 |
| 145.5 | 140.1 |
| 143.8 | 138.4 |
| 141.6 | 136.2 |
| 138.8 | 133.4 |
| 136.4 | 131 |
| 134.9 | 129.5 |
| 131.5 | 126.1 |
| 105.7 | 100.3 |
| 102.1 | 96.7 |
| 95.4 | 90 |
| 65.8 | 60.4 |
| 61.9 | 56.5 |
| 59.8 | 54.4 |
| 53.7 | 48.3 |
| 36.2 | 30.8 |
| 30.8 | 25.4 |
| 24.7 | 19.3 |
| 15.7 | 10.3 |
| 14.4 | 9 |
| 10.1 | 4.7 |
| 8.2 | 2.8 |
| 5.4 | 0. |

45. The N,N-dimethylformamide solvate of tin ethyl etiopurpurin of claim 44 having substantially the solid state NMR spectrum of FIG. 10.

46. The desolvate of the 1,2-dichloroethane solvate of tin ethyl etiopurpurin.

47. The desolvate of the N,N-dimethylformamide solvate of tin ethyl etiopurpurin.

48. The amorphous form of tin ethyl etiopurpurin having an X-ray diffraction pattern with broad peaks at about 10 degrees and about 21 degrees 2θ measured with CuK$_\alpha$ radiation.

49. A process for the preparation of crystalline Form I of tin ethyl etiopurpurin comprising:
  contacting tin ethyl etiopurpurin with a suitable solvent to form a solution thereof; and
  crystallizing tin ethyl etiopurpurin from said solution by evaporating said solvent from said solution under conditions sufficient to yield crystalline Form I of tin ethyl etiopurpurin.

50. The process of claim 49, wherein said solvent is selected from trichloroethane, tetrahydrofuran, and acetone.

51. A process for the preparation of crystalline Form I of tin ethyl etiopurpurin comprising:
  contacting tin ethyl etiopurpurin with a suitable solvent while heating to form a solution thereof; and
  crystallizing tin ethyl etiopurpurin from said solution by cooling said solution under conditions sufficient to yield crystalline Form I of tin ethyl etiopurpurin.

52. The process of claim 51, wherein said solvent is selected from tetrahydrofuran and acetone.

53. A process for the preparation of crystalline Form I of tin ethyl etiopurpurin comprising:
  contacting tin ethyl etiopurpurin with a suitable solvent to form a solution thereof; and
  crystallizing tin ethyl etiopurpurin from said solution by contacting said solution with a suitable antisolvent under conditions sufficient to cause crystalline Form I of tin ethyl etiopurpurin to precipitate from said solution.

54. The process of claim 53, wherein said solvent/antisolvent combinations are selected from dichloromethane/acetone, dichloromethane/acetonitrile, dichloromethane/ethyl acetate, dichloromethane/acetic acid, dichloromethane/hexane, chloroform/acetone, chloroform/acetonitrile, chloroform/ethyl acetate, chloroform/acetic acid, chloroform/hexane, dichloroethane/acetone, dichloroethane/acetonitrile, dichloroethane/ethyl acetate, dichloroethane/acetic acid, and dichloroethane/hexane.

55. A process for the preparation of crystalline Form II of tin ethyl etiopurpurin comprising:
  contacting tin ethyl etiopurpurin with a suitable solvent to form a solution thereof; and
  crystallizing tin ethyl etiopurpurin from said solution by evaporating said solvent from said solution under conditions sufficient to yield crystalline Form II of tin ethyl etiopurpurin.

56. The process of claim 55, wherein said solvent is selected from methanol, dichloromethane, and acetonitrile.

57. A process for the preparation of crystalline Form II of tin ethyl etiopurpurin comprising:
  contacting tin ethyl etiopurpurin with a suitable solvent while heating to form a solution thereof; and
  crystallizing tin ethyl etiopurpurin from said solution by cooling said solution under conditions sufficient to yield crystalline Form II of tin ethyl etiopurpurin.

58. The process of claim 57, wherein said solvent is acetonitrile.

59. A process for the preparation of crystalline Form II of tin ethyl etiopurpurin comprising:
  contacting tin ethyl etiopurpurin with dichloromethane to form a slurry thereof;
  evaporating said dichloromethane from said slurry while treating the slurry with acetic acid to form a solid material;
  contacting said solid material with dichloromethane to form a solution thereof; and
  crystallizing tin ethyl etiopurpurin from said solution by evaporating said dichloromethane from said solution while treating the solution with acetone under conditions sufficient to yield crystalline Form II of tin ethyl etiopurpurin.

60. A process for the preparation of crystalline Form II of tin ethyl etiopurpurin comprising:
  contacting crystalline Form I of tin ethyl etiopurpurin with a suitable solvent to form a slurry thereof; and
  agitating said slurry under conditions sufficient to yield crystalline Form II of tin ethyl etiopurpurin.

61. The process of claim 60, wherein said solvent is selected from dichloromethane, acetone, or a mixture thereof.

62. A process for the preparation of crystalline Form II of tin ethyl etiopurpurin comprising:
  contacting a mixture of crystalline Form I of tin ethyl etiopurpurin and crystalline Form II of tin ethyl etiopurpurin with a suitable solvent to form a slurry thereof; and agitating said slurry under conditions sufficient to yield crystalline Form II of tin ethyl etiopurpurin.

63. The process of claim 62, wherein said solvent is selected from dichloromethane, acetone, or a mixture thereof.

64. A process for the preparation of disordered Form II of tin ethyl etiopurpurin comprising:

contacting tin ethyl etiopurpurin with dichloromethane to form a slurry thereof; evaporating said dichloromethane from said slurry while treating the slurry with acetic acid to form a solid material;

contacting said solid material with dichloromethane to form a solution thereof; and crystallizing tin ethyl etiopurpurin from said solution by evaporating said dichloromethane from said solution while treating the solution with acetone under conditions sufficient to yield disordered Form II of tin ethyl etiopurpurin.

65. A process for the preparation of the 1,2-dichloroethane solvate of tin ethyl etiopurpurin comprising:

contacting tin ethyl etiopurpurin with 1,2-dichloroethane to form a mixture thereof; and evaporating said 1,2-dichloroethane from said mixture under conditions sufficient to yield the 1,2-dichloroethane solvate of tin ethyl etiopurpurin.

66. A process for the preparation of the N,N-dimethylformamide solvate of tin ethyl etiopurpurin comprising:

contacting tin ethyl etiopurpurin with a suitable solvent to form a solution thereof; and treating said solution with N,N-dimethylformamide under conditions sufficient to cause the N,N-dimethylformamide solvate of tin ethyl etiopurpurin to precipitate from said solution.

67. The process of claim 66, wherein said solvent is selected from a mixture of chloroform and N,N-dimethylformamide or a mixture of dichloroethane and N,N-dimethylformamide.

68. A process for preparing amorphous tin ethyl etiopurpurin comprising grinding a solid form of tin ethyl etiopurpurin under conditions which produce the amorphous form.

69. A process for preparing amorphous tin ethyl etiopurpurin comprising:

forming a solution of tin ethyl etiopurpurin in an appropriate solvent; and freeze drying, quench cooling, rapid evaporation or rapid cooling said solution under conditions sufficient to produce the amorphous form of tin ethyl etiopurpurin.

70. A tablet comprising crystalline Form I, crystalline Form II, disordered Form II, desolvates of the 1,2-dichloroethane solvate, desolvates of the N,N-dimethylformamide solvate or amorphous tin ethyl etiopurpurin or mixtures thereof together with at least one inert pharmaceutically acceptable carrier or diluent.

71. A capsule comprising crystalline Form I, crystalline Form II, disordered Form II, desolvates of the 1,2-dichloroethane solvate, desolvates of the N,N-dimethylformamide solvate or amorphous tin ethyl etiopurpurin or mixtures thereof together with at least one inert pharmaceutically acceptable carrier or diluent.

72. A powder comprising crystalline Form I, crystalline Form II, disordered Form II, desolvates of the 1,2-dichloroethane solvate, desolvates of the N,N-dimethylformamide solvate or amorphous tin ethyl etiopurpurin or mixtures thereof together with at least one inert pharmaceutically acceptable carrier or diluent.

73. A lozenge comprising crystalline Form I, crystalline Form II, disordered Form II, desolvates of the 1,2-dichloroethane solvate, desolvates of the N,N-dimethylformamide solvate or amorphous tin ethyl etiopurpurin or mixtures thereof together with at least one inert pharmaceutically acceptable carrier or diluent.

74. A suppository comprising crystalline Form I, crystalline Form II, disordered Form II, desolvates of the 1,2-dichloroethane solvate, desolvates of the N,N-dimethylformamide solvate or amorphous tin ethyl etiopurpurin or mixtures thereof together with at least one inert pharmaceutically acceptable carrier or diluent.

75. An ointment comprising crystalline Form I, crystalline Form II, disordered Form II, desolvates of the 1,2-dichloroethane solvate, desolvates of the N,N-dimethylformamide solvate or amorphous tin ethyl etiopurpurin or mixtures thereof together with at least one inert pharmaceutically acceptable carrier or diluent.

76. A patch or other controlled release device comprising crystalline Form I, crystalline Form II, disordered Form II, desolvates of the 1,2-dichloroethane solvate, desolvates of the N,N-dimethylformamide solvate or amorphous tin ethyl etiopurpurin or mixtures thereof together with at least one inert pharmaceutically acceptable carrier or diluent.

77. A process for producing a solution of tin ethyl etiopurpurin comprising combining crystalline Form I, crystalline Form II, disordered Form II, desolvates of the 1,2-dichloroethane solvate, desolvates of the N,N-dimethylformamide solvate, or amorphous tin ethyl etiopurpurin, or mixtures thereof, with at least one inert pharmaceutically acceptable carrier or diluent.

* * * * *

UNITED STATES PATENT AND TRADEMARK OFFICE
CERTIFICATE OF CORRECTION

PATENT NO.    : 6,605,606 B1
DATED         : August 12, 2003
INVENTOR(S)   : G. Patrick Stahly et al.

It is certified that error appears in the above-identified patent and that said Letters Patent is hereby corrected as shown below:

Column 20,
Line 2, delete "of claim 30".
Line 42, "$CuK_{60}$" should read -- $CuK\alpha$ --.

Signed and Sealed this

Twenty-fifth Day of November, 2003

JAMES E. ROGAN
*Director of the United States Patent and Trademark Office*